US010765680B2

(12) United States Patent
Porter et al.

(10) Patent No.: US 10,765,680 B2
(45) Date of Patent: Sep. 8, 2020

(54) COMBINATION OF A MCL-1 INHIBITOR AND A TAXANE COMPOUND, USES AND PHARMACEUTICAL COMPOSITIONS THEREOF

(71) Applicants: LES LABORATOIRES SERVIER, Suresnes (FR); NOVARTIS AG, Basel (CH)

(72) Inventors: Dale Porter, Cambridge, MA (US); Ensar Halilovic, Canton, MA (US); Maïa Chanrion, Issy les Moulineaux (FR); Ana Leticia Maragno, Croissy-sur-Seine (FR); Olivier Geneste, Rueil-Malmaison (FR); Delphine Merino, Fitzroy (AU); James Whittle, Fitzroy North (AU); François Vaillant, Geelong West (AU); Jane Visvader, Kew (AU); Geoffrey Lindeman, Kew (AU); Guillaume Lessene, Bundoora (AU); Elisabetta Marangoni, Paris (FR)

(73) Assignees: LES LABORATORIES SERVIER, Suresnes (FR); NOVARTIS AG, Basel (CH)

( * ) Notice: Subject to any disclaimer, the term of this patent is extended or adjusted under 35 U.S.C. 154(b) by 0 days.

(21) Appl. No.: 16/475,389

(22) PCT Filed: Jan. 5, 2018

(86) PCT No.: PCT/EP2018/050298
§ 371 (c)(1),
(2) Date: Jul. 2, 2019

(87) PCT Pub. No.: WO2018/127575
PCT Pub. Date: Jul. 12, 2018

(65) Prior Publication Data
US 2019/0336505 A1 Nov. 7, 2019

Related U.S. Application Data

(60) Provisional application No. 62/443,082, filed on Jan. 6, 2017, provisional application No. 62/527,360, filed on Jun. 30, 2017.

(30) Foreign Application Priority Data

Feb. 24, 2017 (EP) ..................................... 17157779

(51) Int. Cl.
*A61K 31/519* (2006.01)
*A61K 9/00* (2006.01)
*A61K 31/337* (2006.01)
*A61P 35/00* (2006.01)

(52) U.S. Cl.
CPC .......... *A61K 31/519* (2013.01); *A61K 9/0019* (2013.01); *A61K 9/0053* (2013.01); *A61K 31/337* (2013.01); *A61P 35/00* (2018.01)

(58) Field of Classification Search
CPC .. A61K 31/519; A61K 9/0019; A61K 9/0053; A61K 9/337; A61P 35/00
USPC ...................................................... 514/260.1
See application file for complete search history.

(56) References Cited

U.S. PATENT DOCUMENTS

| | | | | |
|---|---|---|---|---|
| 9,670,227 B2 * | 6/2017 | Kotschy | ............ | A61K 31/5377 |
| 10,227,358 B2 * | 3/2019 | Szlavik | ............... | C07D 495/04 |
| 10,278,972 B2 * | 5/2019 | Kotschy | ............... | C07D 495/04 |
| 10,322,131 B2 * | 6/2019 | Szlavik | ............... | A61K 31/519 |
| 10,323,041 B2 * | 6/2019 | Balint | ................... | C07D 333/56 |
| 10,457,687 B2 * | 10/2019 | Szlavik | ................... | A61P 35/00 |
| 10,457,689 B2 * | 10/2019 | Paczal | ................... | A61K 45/06 |
| 2015/0352097 A1 * | 12/2015 | Cardone | ............. | A61K 31/496 |
| | | | | 514/253.06 |
| 2019/0206648 A1 * | 7/2019 | Yosui | ................... | H02K 41/031 |

FOREIGN PATENT DOCUMENTS

| | | | |
|---|---|---|---|
| CN | 105311016 | 2/2016 | |
| EP | 2886545 | 6/2015 | |
| WO | WO2016207216 | 12/2016 | |
| WO | WO2016207217 | 12/2016 | |
| WO | WO-2016207217 A1 * | 12/2016 | ........... C07D 403/12 |
| WO | WO2016207226 | 12/2016 | |

OTHER PUBLICATIONS

Horig et al. Journal of Translational Medicine 2004, 2(44), p. 1-6.*
Schafer et al. Drug Discovery Today, 2008, 13 (21/22), 913-916.*
Xiang et al, Onco Targets and Therapy, (2018), 11, p. 7301-7314.*
Wertz et al. Nature, (2011), 471 (7336), p. 110-114.*
Habata, Shutaro, et al., "BAG3-mediated Mcl-1 stabilization contributes to drug resistance via interaction with USP9X in ovarian cancer", International Journal of Oncology, 49, 2015, pp. 402-410.
International Search Report for PCT/EP2018/050296 dated Mar. 23, 2018.
Liu, Xiaopeng, et al., "MicroRNA-101 inhibits cell progression and inceases paclitaxel sensitivity by suppressing MCL-1 expression in human triple-negative breast cancer", Oncotarget, vol. , No. 24, 2015, pp. 20070-20083.
Song, Ting, et al., "Mechanism of synergy of BH3 mimetics and paclitaxel in chronic myeloid leukemia cells: Mcl-1 inhibition", European Journal of Pharmaceutical Sciences, 70, 2015, pp. 64-71.

* cited by examiner

*Primary Examiner* — Yong L Chu
(74) *Attorney, Agent, or Firm* — Hueschen and Sage

(57) ABSTRACT

A combination comprising a MCL-1 inhibitor and a taxane compound, and compositions and uses thereof.

16 Claims, 15 Drawing Sheets

Synergy Score: 14.9

Figure 8
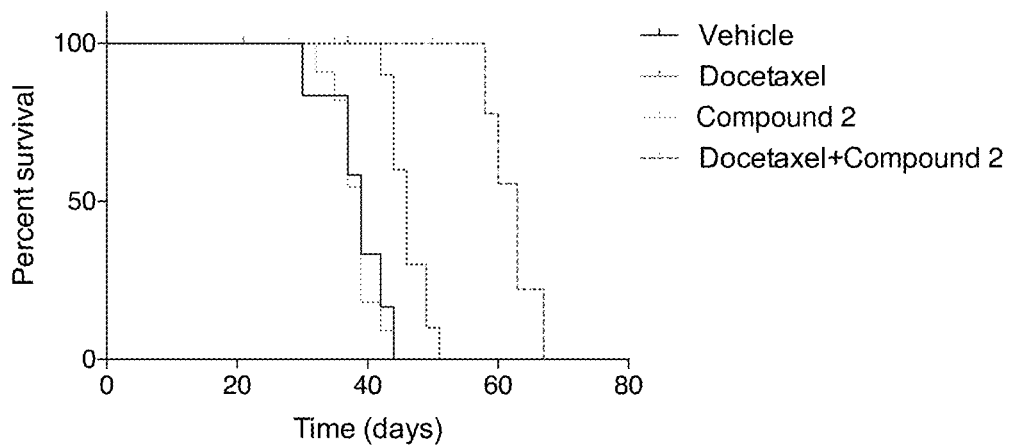
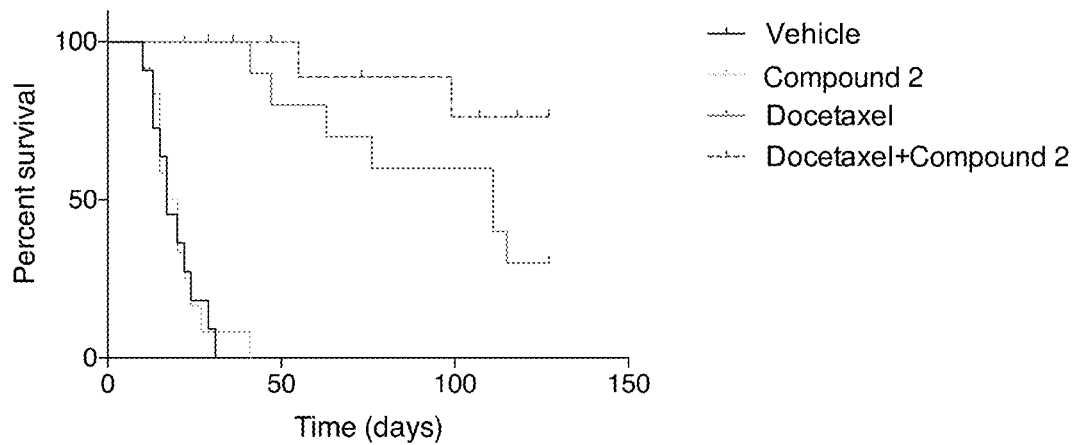
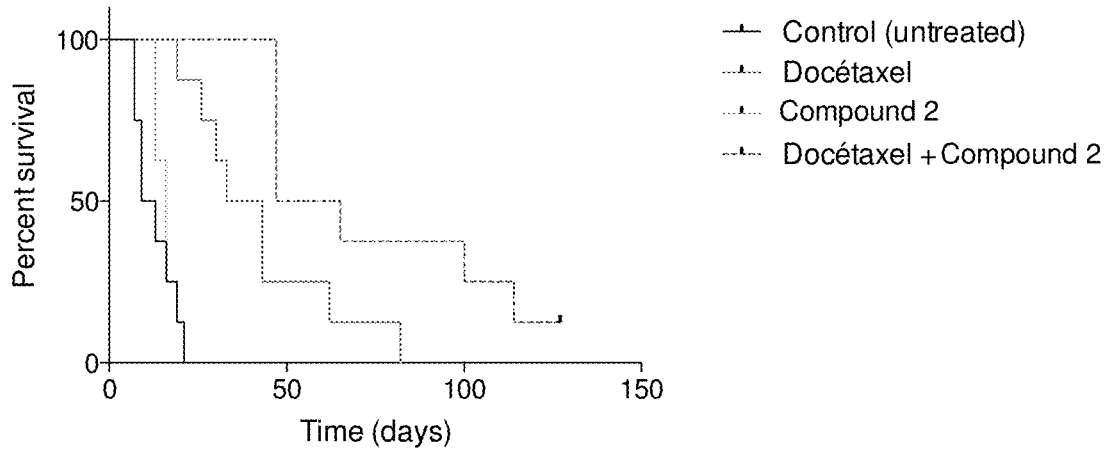

COMBINATION OF A MCL-1 INHIBITOR AND A TAXANE COMPOUND, USES AND PHARMACEUTICAL COMPOSITIONS THEREOF

FIELD OF THE INVENTION

The present invention relates to a combination of a MCL-1 inhibitor and a taxane compound. The invention also relates to the use of said combination in the treatment of cancer, in particular breast, lung, ovarian, bladder and prostate cancers, more particularly breast and lung cancers. Also provided are pharmaceutical formulations suitable for the administration of such combinations.

BACKGROUND OF THE INVENTION

Cancer is characterized by uncontrolled cell proliferation. Antimitotic agents and antimicrotubule agents have been explored for cancer therapy because of their important effect in the cell division. Inhibition of the mitotic machinery results in a diverse array of outcomes, primarily leading to cell cycle arrest and cell death. Antimicrotubule agents, such as taxanes are currently being used in clinical setting. For example, paclitaxel and docetaxel have a similar spectrum of clinical activity including ovarian, lung, breast, bladder, and prostate cancers. Taxanes are anti-mitotic agents that bind to tubulin and inhibit microtubule depolymerization thereby disrupting the normal equilibrium involved in microtubule assembly and deconstruction and therefore impair microtubule functioning. Microtubules are essential to cell division and cells exposed to taxanes can fail to divide. Cell cycle arrest after treatment with taxanes may eventually result in cell death due to unsuccessful mitosis. Despite the advances in anticancer therapy, there exists a long-felt need for more effective therapies with limited toxicities. Indeed, the toxicities associated with paclitaxel and docetaxel include neutropenia as the major dose limiting toxicity, along with significant peripheral neuropathy. In fact, dose reductions are frequent in heavily pretreated patients to mitigate the severity of these toxicities. On top of that, the development of resistance to taxanes also limits its use in the clinic.

Apoptosis is a highly regulated cell death pathway that is initiated by various cytotoxic stimuli, including oncogenic stress and chemotherapeutic agents. It has been shown that evasion of apoptosis is a hallmark of cancer and that efficacy of many chemotherapeutic agents is dependent upon the activation of the intrinsic mitochondrial pathway. Three distinct subgroups of the BCL-2 family proteins control the intrinsic apoptosis pathway: (i) the pro-apoptotic BH3 (the Bcl-2 homology 3)-only proteins; (ii) the pro-survival members such as BCL-2 itself, BCL-xL, BCL-W, MCL-1 and BCL-2A1; and (iii) the pro-apoptotic effector proteins BAX and BAK (Czabotar et al., Nature Reviews Molecular Cell Biology 2014, 15, 49-63). Overexpression of the anti-apoptotic members of BCL-2 family is observed in many cancers, (Adams and Cory, Oncogene 2007, 26, 1324-1337) and the pharmacological inhibition of the anti-apoptotic proteins by BH3-mimetics drugs such as ABT-199 (venetoclax), ABT-263 (navitoclax) and 563845 has emerged as a therapeutic strategy to induce apoptosis and cause tumor regression in cancer (Zhang et al., Drug Resist. Updat. 2007, 10, 207-217; Kotschy et al., Nature 2016, 538, 477-482). Nevertheless, mechanisms of resistance to BH3 mimetics have been observed (Choudhary et al., Cell Death and Disease 2015, 6, e1593) and the use of combination therapies could improve efficacy and delay or even abrogate resistance development.

Breast cancer is a heterogeneous disease and can be stratified into at least five major subgroups based on gene expression profiling: Luminal A, Luminal B (estrogen positive, $ER^+$), HER2-amplified, basal-like (predominantly triple negative breast cancer or TNBC) and normal-like (Curtis et al., Nature 2012, 486, 346-352; Perou et al., Nature 2000, 406, 747-752). These subtypes generally predict clinical behavior with respect to response and resistance to therapy, patterns of metastasis, and overall survival. Multiple mechanisms contribute to tumor progression and resistance to cancer therapy, including the evasion of cell death due to deregulation of the balance between anti- and pro-apoptotic members of the BCL2 family (Merino et al., Oncogene 2016, 35, 1877-1887; Beroukim et al., Nature 2010, 463, 899-905; Wertz et al., Nature 2011, 471, 110-114; Goodwin et al., Cell Death Differ. 2015). In the triple-negative breast cancer subgroup, residual disease after neoadjuvant therapy is associated with higher risk of metastatic recurrence compared to patients achieving a pathological complete response (Liedtke et al., J. Clin. Oncol. 2008, 26(8), 1275-1281). About 70% of TNBC patients do not achieve complete response after neo-adjuvant chemotherapy (such as paclitaxel or docetaxel) and suffer a dramatically worse outcome, with a higher probability of metastatic relapse and a 3-year overall survival of only 60-70%.

Lung cancer is classified into non-small cell lung cancer (NSCLC), small cell lung cancer (SCLC), and carcinoid. Approximately 80% of all lung cancers correspond to NSCLC, which can be further classified into adenocarcinoma, squamous cell carcinoma, and large cell carcinoma. Lung cancer is the most common cause of cancer-related death in men and second most common in women after breast cancer. Although lung cancer therapy has evolved significantly with the appearance of targeted therapy, there is still a strong need to develop novel therapies in order to improve treatment efficacy, reduce side effects and avoid appearance of resistance (Rothschild Cancers 2015, 7(2), 930-949).

The present invention provides a novel combination of a MCL-1 inhibitor and a taxane compound. The results show that with the association of potent small molecules targeting MCL-1 with antimicrotubule agents is highly synergistic in breast and lung cancer cell lines (FIGS. 1 to 7; Tables 1 and 4). We also show that combined disrupting microtubule function and MCL-1 targeting in vivo is efficacious at tolerated doses in breast cancer PDX (Patient Derived Xenograft) models (FIGS. 8 and 9) and at different doses in female nude rats bearing MDA-MB-231 xenograft, a model of triple negative breast cancer (FIGS. 10 to 14). The positive combination was also observed on different PDX models of TNBC using different schedules of administration (FIG. 15). The synergistic effect of targeting MCL-1 and disrupting microtubule function in vitro and in vivo at tolerated doses have been demonstrated through combination of potent small molecule inhibitors. Finally, residual tumor analysis after neo-adjuvant treatment is a major and under-explored field to study chemoresistance and, thus, we perform experiments in PDX models resistant to chemotherapy showing that the combination of a MCL-1 inhibitor and a taxane compound is efficient (Example 9).

SUMMARY OF THE INVENTION

The present invention relates to a combination comprising:

(a) a MCL-1 inhibitor of formula (I):

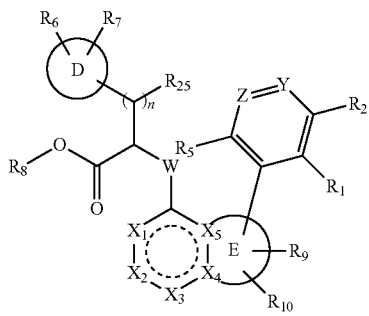

wherein:
D represents a cycloalkyl group, a heterocycloalkyl group, an aryl group or a heteroaryl group,
E represents a furyl, thienyl or pyrrolyl ring,
$X_1$, $X_3$, $X_4$ and $X_5$ independently of one another represent a carbon atom or a nitrogen atom,
$X_2$ represents a C—$R_{26}$ group or a nitrogen atom,

means that the ring is aromatic,
Y represents a nitrogen atom or a C—$R_3$ group,
Z represents a nitrogen atom or a C—$R_4$ group,
$R_1$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl group, a cyano group, a nitro group, -$Cy_3$, -alkyl($C_0$-$C_6$)—$NR_{11}R_{11}'$, —O-alkyl($C_1$-$C_6$)—$NR_{11}R_{11}'$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$),
$R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-Cy), -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$NR_{11}R_{11}'$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$),
or the substituents of the pair ($R_1$, $R_2$), ($R_2$, $R_3$), ($R_3$, $R_4$), ($R_4$, $R_5$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by from 1 to 2 groups selected from halogen, linear or branched ($C_1$-$C_6$)alkyl, -alkyl($C_0$-$C_6$)—$NR_{11}R_{11}'$, —$NR_{13}R_{13}'$, -alkyl($C_0$-$C_6$)-$Cy_1$ or oxo,
$R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-alkyl($C_1$-$C_6$)—$NR_{11}R_{11}'$, —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$),
or the substituents of the pair ($R_6$, $R_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{13}R_{13}'$, -alkyl($C_0$-$C_6$)-$Cy_1$ or an oxo,
W represents a —$CH_2$— group, a —NH— group or an oxygen atom,
$R_8$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group,
$R_9$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, -$Cy_2$, -alkyl($C_1$-$C_6$)-$Cy_2$, -alkenyl($C_2$-$C_6$)-$Cy_2$, -alkynyl($C_2$-$C_6$)-$Cy_2$, -$Cy_2$-$Cy_3$, -alkynyl($C_2$-$C_6$)—O-$Cy_2$, -$Cy_2$-alkyl($C_0$-$C_6$)—O-alkyl($C_0$-$C_6$)-$Cy_3$, a halogen atom, a cyano group, —C(O)—$R_{14}$, or —C(O)—$NR_{14}R_{14}'$,
$R_{10}$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, an arylalkyl($C_1$-$C_6$) group, a cycloalkylalkyl($C_1$-$C_6$) group, a linear or branched ($C_1$-$C_6$)polyhaloalkyl, or -alkyl($C_1$-$C_6$)—O-$Cy_4$,
or the substituents of the pair ($R_9$, $R_{10}$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen,
$R_{11}$ and $R_{11}'$ independently of one another represent a hydrogen atom, an optionally substituted linear or branched ($C_1$-$C_6$)alkyl group, or -alkyl($C_0$-$C_6$)-$Cy_1$,
or the substituents of the pair ($R_{11}$, $R_{11}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by from 1 to 2 groups representing a hydrogen atom, or a linear or branched ($C_1$-$C_6$)alkyl group and it being understood that one or more of the carbon atoms of the possible substituents, may be deuterated,
$R_{12}$ represents -$Cy_5$, -$Cy_5$-alkyl($C_0$-$C_6$)—O-alkyl($C_0$-$C_6$)-$Cy_6$, -$Cy_5$-alkyl($C_0$-$C_6$)-$Cy_6$, -$Cy_5$-alkyl($C_0$-$C_6$)—

$NR_{11}$-alkyl($C_0$-$C_6$)-$Cy_6$, -$Cy_5$-$Cy_6$-O-alkyl($C_0$-$C_6$)-$Cy_7$, -$Cy_5$-alkyl($C_0$-$C_6$)—O-alkyl($C_0$-$C_6$)-$Cy_9$, -$Cy_5$-alkyl($C_0$-$C_6$)-$Cy_9$, —NH—C(O)—NH—$R_{11}$, -$Cy_5$-alkyl($C_0$-$C_6$)—$NR_{11}$-alkyl($C_0$-$C_6$)-$Cy_9$, —C(O)—$NR_{11}R_{11}'$, —$NR_{11}R_{11}'$, —$OR_{11}$, —$NR_{11}$—C(O)—$R_{11}'$, —O-alkyl($C_1$-$C_6$)—$OR_{11}$, —$SO_2$—$R_{11}$, —C(O)—$OR_{11}$,

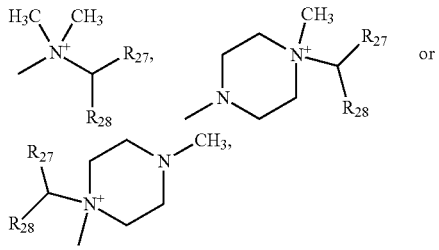

it being possible for the ammonium so defined to exist as a zwitterionic form or to have a monovalent anionic counterion, $R_{13}$, $R_{13}'$, $R_{14}$ and $R_{14}'$ independently of one another represent a hydrogen atom, or an optionally substituted linear or branched ($C_1$-$C_6$)alkyl group, $R_a$ represents a hydrogen atom or a linear or branched ($C_1$-$C_6$)alkyl group, $R_b$ represents a —O—C(O)—O—$R_c$ group, a —O—C(O)—$NR_cR_c'$ group, or a —O—P(O)($OR_c$)$_2$ group, $R_c$ and $R_c'$ independently of one another represent a hydrogen atom, a linear or branched ($C_1$-$C_8$)alkyl group, a cycloalkyl group, a ($C_1$-$C_6$)alkoxy($C_1$-$C_6$)alkyl group, or a ($C_1$-$C_6$)alkoxycarbonyl($C_1$-$C_6$)alkyl group, or the substituents of the pair ($R_c$, $R_c'$) form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched ($C_1$-$C_6$)alkyl group, $Cy_1$, $Cy_2$, $Cy_3$, $Cy_4$, $Cy_5$, $Cy_6$, $Cy_7$, $Cy_8$ and $Cy_{10}$ independently of one another, represent a cycloalkyl group, a heterocycloalkyl group, an aryl group or a heteroaryl group, $Cy_9$ represents

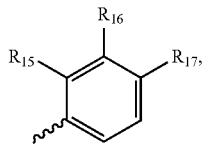

or $Cy_9$ represents a heteroaryl group which is substituted by a group selected from —O—P(O)($OR_{20}$)$_2$; —O—P(O)($O^-M^+$)$_2$; —($CH_2$)$_p$—O—($CHR_{18}$—$CHR_{19}$—O)$_q$—$R_{20}$; hydroxy; hydroxy($C_1$-$C_6$)alkyl; —($CH_2$)$_r$—U—($CH_2$)$_s$-heterocycloalkyl; or —U—($CH_2$)$_q$—$NR_{21}R_{21}'$, $R_{15}$ represents a hydrogen atom; a —($CH_2$)$_p$—O—($CHR_{18}$—$CHR_{19}$—O)$_q$—$R_{20}$ group; a linear or branched ($C_1$-$C_6$)alkoxy($C_1$-$C_6$)alkyl group; a —U—($CH_2$)$_q$—$NR_{21}R_{21}'$ group; or a —($CH_2$)$_r$—U—($CH_2$)$_s$-heterocycloalkyl group, $R_{16}$ represents a hydrogen atom; a hydroxy group; a hydroxy($C_1$-$C_6$)alkyl group;
a —($CH_2$)$_r$—U—($CH_2$)$_s$-heterocycloalkyl group; a ($CH_2$)$_r$—U—V—O—P(O)($OR_{20}$)$_2$ group;
a —O—P(O)($O^-M^+$)$_2$ group; a —($CH_2$)$_p$—O—($CHR_{18}$—$CHR_{19}$—O)$_q$—$R_{20}$ group;
a —($CH_2$)$_p$—O—C(O)—$NR_{22}R_{23}$ group; or a —U—($CH_2$)$_q$—$NR_{21}R_{21}'$ group, $R_{17}$ represents a hydrogen atom; a —($CH_2$)$_p$—O—($CHR_{18}$—$CHR_{19}$—O)$_q$—$R_{20}$ group;
a —O—P(O)($OR_{20}$)$_2$ group; a —O—P(O)($O^-M^+$)$_2$ group; a hydroxy group;
a hydroxy($C_1$-$C_6$)alkyl group; a —($CH_2$)$_r$—U—($CH_2$)$_s$-heterocycloalkyl group;
a —U—($CH_2$)$_q$—$NR_{21}R_{21}'$ group; or an aldonic acid, $M^+$ represents a pharmaceutically acceptable monovalent cation, U represents a bond or an oxygen atom, V represents a —($CH_2$)$_s$— group or a —C(O)— group, $R_{18}$ represents a hydrogen atom or a ($C_1$-$C_6$)alkoxy($C_1$-$C_6$)alkyl group, $R_{19}$ represents a hydrogen atom or a hydroxy($C_1$-$C_6$)alkyl group, $R_{20}$ represents a hydrogen atom or a linear or branched ($C_1$-$C_6$)alkyl group, $R_{21}$ and $R_{21}'$ independently of one another represent a hydrogen atom, a linear or branched ($C_1$-$C_6$)alkyl group, or a hydroxy($C_1$-$C_6$)alkyl group, or the substituents of the pair ($R_{21}$, $R_{21}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the resulting ring may be substituted by a group representing a hydrogen atom or a linear or branched ($C_1$-$C_6$) alkyl group, $R_{22}$ represents a ($C_1$-$C_6$)alkoxy($C_1$-$C_6$)alkyl group, a —($CH_2$)$_p$—$NR_{24}R_{24}'$ group, or a —($CH_2$)$_p$—O—($CHR_{18}$—$CHR_{19}$—O)$_q$—$R_{20}$ group, $R_{23}$ represents a hydrogen atom or a ($C_1$-$C_6$)alkoxy($C_1$-$C_6$)alkyl group, or the substituents of the pair ($R_{22}$, $R_{23}$) form together with the nitrogen atom carrying them an aromatic or non-aromatic ring composed of from 5 to 18 ring members, which may contain in addition to the nitrogen atom from 1 to 5 heteroatoms selected from oxygen, sulphur and nitrogen, it being understood that the resulting ring may be substituted by a group representing a hydrogen atom, a linear or branched ($C_1$-$C_6$)alkyl group or a heterocycloalkyl group, $R_{24}$ and $R_{24}'$ independently of one another represent a hydrogen atom or a linear or branched ($C_1$-$C_6$)alkyl group, or the substituents of the pair ($R_{24}$, $R_{24}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the resulting ring may be substituted by a group representing a hydrogen atom or a linear or branched ($C_1$-$C_6$) alkyl group, $R_{25}$ represents a hydrogen atom, a hydroxy group, or a hydroxy($C_1$-$C_6$)alkyl group, $R_{26}$ represents a hydrogen atom, a halogen atom, a linear or branched ($C_1$-$C_6$)alkyl group, or a cyano group, R$_{27}$ represents a hydrogen atom or a linear or branched (C$_1$-C$_6$)alkyl group, R$_{28}$ represents a —O—P(O)(O$^-$)(O$^-$) group, a —O—P(O)(O$^-$)(OR$_{30}$) group,
a —O—P(O)(OR$_{30}$)(OR$_{30}$') group, a —O—SO$_2$—O$^-$ group, a —O—SO$_2$—OR$_{30}$ group, -Cy$_{10}$,
a —O—C(O)—R$_{29}$ group, a —O—C(O)—OR$_{29}$ group or a —O—C(O)—NR$_{29}$R$_{29}$' group;

R$_{29}$ and R$_{29}$' independently of one another represent a hydrogen atom, a linear or branched (C$_1$-C$_6$)alkyl group or a linear or branched amino(C$_1$-C$_6$)alkyl group, R$_{30}$ and R$_{30}$' independently of one another represent a hydrogen atom, a linear or branched (C$_1$-C$_6$)alkyl group or an arylalkyl(C$_1$-C$_6$) group, n is an integer equal to 0 or 1,
p is an integer equal to 0, 1 or 2,
q is an integer equal to 1, 2, 3 or 4,
r and s are independently an integer equal to 0 or 1,
it being understood that:
"aryl" means a phenyl, naphthyl, biphenyl, indanyl or indenyl group,
"heteroaryl" means any mono- or bi-cyclic group composed of from 5 to 10 ring members, having at least one aromatic moiety and containing from 1 to 3 heteroatoms selected from oxygen, sulphur and nitrogen,
"cycloalkyl" means any mono- or bi-cyclic non-aromatic carbocyclic group containing from 3 to 10 ring members,
"heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched (C$_1$-C$_6$)alkyl, optionally substituted linear or branched (C$_2$-C$_6$)alkenyl group, optionally substituted linear or branched (C$_2$-C$_6$)alkynyl group, optionally substituted linear or branched (C$_1$-C$_6$)alkoxy, optionally substituted (C$_1$-C$_6$) alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched (C$_1$-C$_6$)polyhaloalkyl, trifluoromethoxy, or halogen, it being understood that R' and R" independently of one another represent a hydrogen atom or an optionally substituted linear or branched (C$_1$-C$_6$)alkyl group, and it being understood that one or more of the carbon atoms of the preceding possible substituents, may be deuterated, or their enantiomers, diastereoisomers, atropisomers, or addition salts thereof with a pharmaceutically acceptable acid or base, and (b) a taxane compound,
for simultaneous, sequential or separate use.

Said compounds of formula (I), their synthesis, their use in the treatment of cancer and pharmaceutical formulations thereof, are described in WO 2015/097123, WO 2016/207216, WO 2016/207217, WO 2016/207225, WO 2016/207226 and WO 2017/125224, the contents of which are incorporated by reference.

In certain embodiments, the taxane compound is selected from paclitaxel, docetaxel, cabazitaxel, tesetaxel, Opaxio® (paclitaxel poliglumex), Abraxane® (nab-paclitaxel) larotaxel, taxoprexin, BMS-184476, hongdoushan A, hongdoushan B, and hongdoushan C, and others.

According to a first aspect of the invention, there is provided a combination comprising:
(a) a MCL-1 inhibitor of formula (II), a particular case of MCL-1 inhibitor of formula (I):

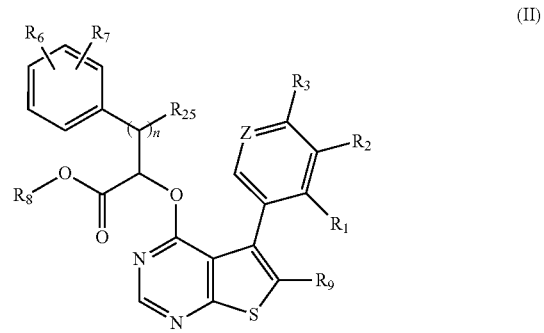

(II)

wherein:
Z represents a nitrogen atom or a C—R$_4$ group,
R$_1$ represents a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)alkoxy group, —S—(C$_1$-C$_6$)alkyl group, a linear or branched (C$_1$-C$_6$)polyhaloalkyl, a hydroxy group, a cyano, —NR$_{11}$R$_{11}$', -Cy$_8$ or a halogen atom,
R$_2$, R$_3$ and R$_4$ independently of one another represent a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a linear or branched (C$_1$-C$_6$)alkoxy group, —S—(C$_1$-C$_6$)alkyl group, a cyano group, a nitro group, -alkyl(C$_0$-C$_6$)—NR$_{11}$R$_{11}$', —O-Cy$_1$, -alkyl(C$_0$-C$_6$)-Cy$_1$, -alkenyl(C$_2$-C$_6$)-Cy$_1$, -alkynyl(C$_2$-C$_6$)-Cy$_1$, —O-alkyl(C$_1$-C$_6$)—R$_{12}$, —C(O)—OR$_{11}$, —O—C(O)—R$_{11}$, —C(O)—NR$_{11}$R$_{11}$', —NR$_{11}$—C(O)—R$_{11}$', —NR$_{11}$—C(O)—OR$_{11}$', -alkyl(C$_1$-C$_6$)—NR$_{11}$—C(O)—R$_{11}$', —SO$_2$—NR$_{11}$R$_{11}$', or —SO$_2$-alkyl(C$_1$-C$_6$),
or the substituents of one of the pairs (R$_2$, R$_3$), (R$_3$, R$_4$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched (C$_1$-C$_6$)alkyl group, —NR$_{13}$R$_{13}$', -alkyl(C$_0$-C$_6$)-Cy$_1$ or an oxo,
R$_6$ and R$_7$ independently of one another represent a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a linear or branched (C$_1$-C$_6$)alkoxy group, a —S—(C$_1$-C$_6$)alkyl group, a cyano group, a nitro group, -alkyl(C$_0$-C$_6$)—NR$_{11}$R$_{11}$', —O-Cy$_1$, -alkyl(C$_0$-C$_6$)-Cy$_1$, -alkenyl(C$_2$-C$_6$)-Cy$_1$, -alkynyl(C$_2$-C$_6$)-Cy$_1$, —O-alkyl(C$_1$-C$_6$)—R$_{12}$, —C(O)—OR$_{11}$, —O—C(O)—R$_{11}$, —C(O)—NR$_{11}$R$_{11}$', —NR$_{11}$—C(O)—R$_{11}$', —NR$_{11}$—C(O)—OR$_{11}$', -alkyl(C$_1$-C$_6$)—NR$_{11}$—C(O)—R$_{11}$', —SO$_2$—NR$_{11}$R$_{11}$', or —SO$_2$-alkyl(C$_1$-C$_6$),
or the substituents of the pair (R$_6$, R$_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched $(C_1-C_6)$alkyl group, —$NR_{13}R_{13}'$, -alkyl$(C_0-C_6)$-$Cy_1$ or an oxo, $R_8$ represents a hydrogen atom, a linear or branched $(C_1-C_8)$alkyl group, an aryl group, a heteroaryl group, an arylalkyl$(C_1-C_6)$ group, or a heteroarylalkyl$(C_1-C_6)$ group, $R_9$ represents a linear or branched $(C_1-C_6)$alkyl group, a linear or branched $(C_2-C_6)$alkenyl group, a linear or branched $(C_2-C_6)$alkynyl group, -$Cy_2$, -alkyl$(C_1-C_6)$-$Cy_2$, -alkenyl$(C_2-C_6)$-$Cy_2$, -alkynyl$(C_2-C_6)$-$Cy_2$, -$Cy_2$-$Cy_3$, -alkynyl$(C_2-C_6)$—O-$Cy_2$, -$Cy_2$-alkyl$(C_0-C_6)$—O-alkyl$(C_0-C_6)$-$Cy_3$, a halogen atom, a cyano group, —C(O)—$R_{14}$, or —C(O)—$NR_{14}R_{14}'$, $R_{11}$ and $R_{11}'$ independently of one another represent a hydrogen atom, an optionally substituted linear or branched $(C_1-C_6)$alkyl group, or -alkyl$(C_0-C_6)$-$Cy_1$, or the substituents of the pair $(R_{11}, R_{11}')$ form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom, or a linear or branched $(C_1-C_6)$alkyl group and it being understood that one or more of the carbon atoms of the possible substituents, may be deuterated, $R_{12}$ represents -$Cy_5$, -$Cy_5$-alkyl$(C_0-C_6)$-$Cy_6$, -$Cy_5$-alkyl$(C_0-C_6)$—O-alkyl$(C_0-C_6)$-$Cy_6$, -$Cy_5$-alkyl$(C_0-C_6)$—$NR_{11}$-alkyl$(C_0-C_6)$-$Cy_6$, -$Cy_5$-$Cy_6$-O-alkyl$(C_0-C_6)$-$Cy_7$, —C(O)—$NR_{11}R_{11}'$, —$NR_{11}R_{11}'$, —$OR_{11}$, —$NR_{11}$—C(O)—$R_{11}'$, —O-alkyl$(C_1-C_6)$—$OR_{11}$, —$SO_2$—$R_{11}$, —C(O)—$OR_{11}$, or —NH—C(O)—NH—$R_{11}$, $R_{13}$, $R_{13}'$, $R_{14}$ and $R_{14}'$ independently of one another represent a hydrogen atom, or an optionally substituted linear or branched $(C_1-C_6)$alkyl group, $R_{25}$ represents a hydrogen atom, a hydroxy group, or a hydroxy$(C_1-C_6)$alkyl group, $Cy_1$, $Cy_2$, $Cy_3$, $Cy_5$, $Cy_6$, $Cy_7$ and $Cy_8$ independently of one another, represent a cycloalkyl group, a heterocloalkyl group, an aryl group or a heteroaryl group, n is an integer equal to 0 or 1, it being understood that:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched $(C_1-C_6)$alkyl, optionally substituted linear or branched $(C_2-C_6)$alkenyl group, optionally substituted linear or branched $(C_2-C_6)$alkynyl group, optionally substituted linear or branched $(C_1-C_6)$alkoxy, optionally substituted $(C_1-C_6)$ alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched $(C_1-C_6)$polyhaloalkyl, trifluoromethoxy, or halogen, it being understood that R' and R" independently of one another represent a hydrogen atom or an optionally substituted linear or branched $(C_1-C_6)$alkyl group, and it being understood that one or more of the carbon atoms of the preceding possible substituents, may be deuterated, or their enantiomers, diastereoisomers, atropisomers, or addition salts thereof with a pharmaceutically acceptable acid or base, and (b) a taxane compound, for simultaneous, sequential or separate use.

In another embodiment, the invention provides a combination comprising:

(a) a MCL-1 inhibitor of formula (I) as described herein, and (b) a taxane compound selected from paclitaxel or docetaxel, or (a) a MCL-1 inhibitor of formula (II) as described herein, and (b) a taxane compound selected from paclitaxel or docetaxel, for simultaneous, sequential or separate use.

In another embodiment, the invention provides a combination comprising:

(a) Compound 1: (2R)-2-{[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, or a pharmaceutically acceptable salt thereof, and (b) a taxane compound, for simultaneous, sequential or separate use.

Alternatively, the invention provides a combination comprising:

(a) Compound 2: (2R)-2-{[(5S$_a$)-5-{3-chloro-2-methyl-4-[2-(4-methylpiperazin-1-yl) ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl) propanoic acid, or a pharmaceutically acceptable salt thereof, and (b) a taxane compound, for simultaneous, sequential or separate use.

In another embodiment, the invention provides a combination as described herein, for use in the treatment of cancer.

In another embodiment, the invention provides the use of a combination as described herein, in the manufacture of a medicament for the treatment of cancer.

In another embodiment, the invention provides a medicament containing, separately or together, (a) a MCL-1 inhibitor of formula (I) as described herein, and (b) a taxane compound, or (a) a MCL-1 inhibitor of formula (II) as described herein, and (b) a taxane compound, for simultaneous, sequential or separate administration, and wherein the MCL-1 inhibitor and the taxane compound are provided in effective amounts for the treatment of cancer.

In another embodiment, the invention provides a method of treating cancer, comprising administering a jointly therapeutically effective amount of:

(a) a MCL-1 inhibitor of formula (I) as described herein, and (b) a taxane compound,
or
(a) a MCL-1 inhibitor of formula (II) as described herein, and
(b) a taxane compound,
to a subject in need thereof.

In another embodiment, the MCL-1 inhibitor is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid (Compound 1).

In another embodiment, the MCL-1 inhibitor is (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid (Compound 2).

In another embodiment, the taxane compound is paclitaxel.

In another embodiment, the taxane compound is docetaxel.

BRIEF DESCRIPTION OF THE FIGURES

FIG. 8 illustrates efficacy of Compound 2 with docetaxel in improving of animal survival in TNBC PDX models. Kaplan-Meier survival curves of mice bearing 110T (n=10-12 mice per arm), 838T (n=12 mice per arm), or PDX OD-BRE-0589 (8 mice per arm) treated with vehicle alone (black line), docetaxel (10 mg/kg i.p. on day 0 and 21) plus vehicle for Compound 2 (dark grey line), Compound 2 (25 mg/kg i.v. once weekly for 6 weeks) plus vehicle for docetaxel (light grey line), or combined docetaxel and Compound 2 (dotted line). Right panels: individual tumor volume curves. The PDX 838T model was terminated at 120 days due to age related illness, independent of therapy. Log rank (Mantel-Cox) p value is showing for combination therapy versus docetaxel alone.

DETAILED DESCRIPTION OF THE INVENTION

Figure 1:
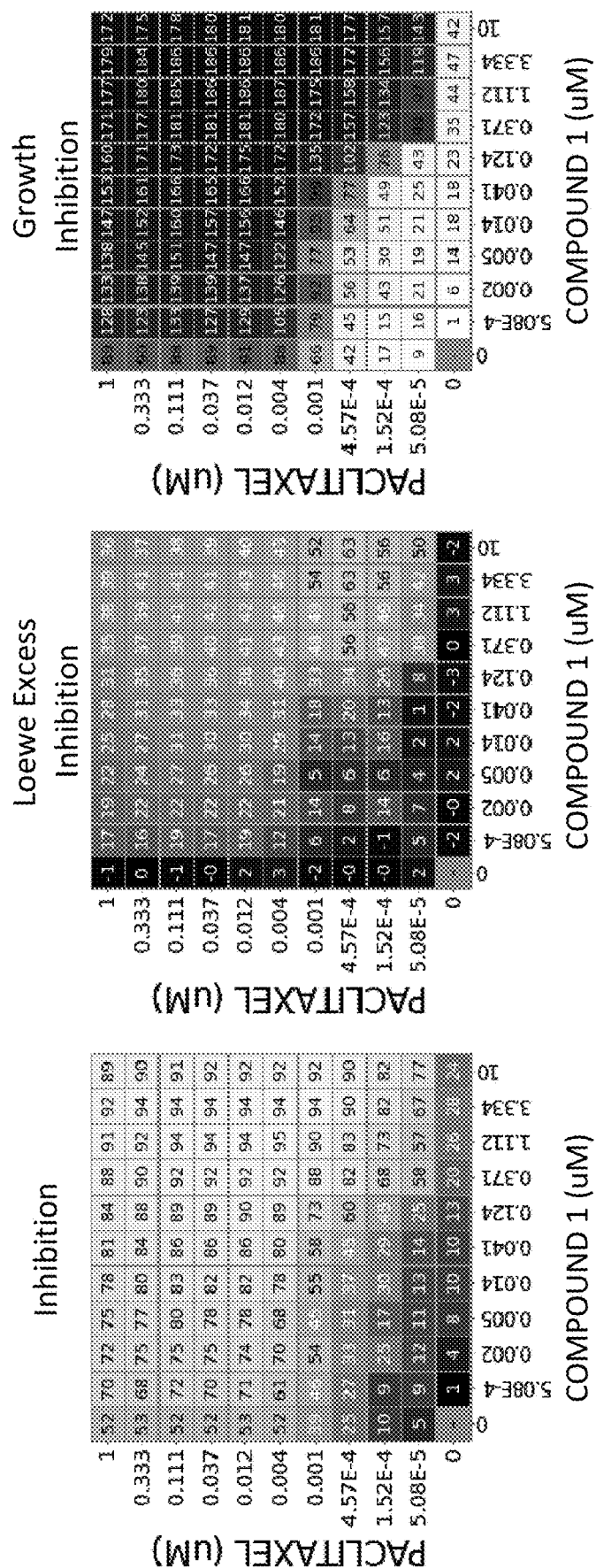
FIG. 1 illustrates matrices for inhibition, Loewe excess inhibition and growth inhibition for paclitaxel combinations with Compound 1 in representative MDA-MB-453 breast cancer cell line.

The invention therefore provides in Embodiment E1, a combination comprising:

(a) a MCL-1 inhibitor of formula (I):

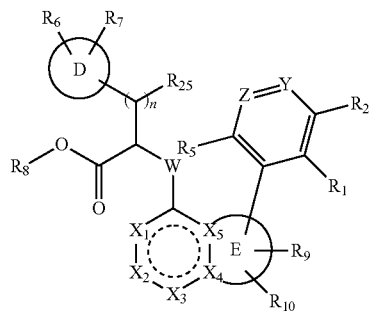

(I)

wherein:
D represents a cycloalkyl group, a heterocycloalkyl group, an aryl group or a heteroaryl group,
E represents a furyl, thienyl or pyrrolyl ring,
$X_1$, $X_3$, $X_4$ and $X_5$ independently of one another represent a carbon atom or a nitrogen atom,
$X_2$ represents a C—$R_{26}$ group or a nitrogen atom,

means that the ring is aromatic,
Y represents a nitrogen atom or a C—$R_3$ group,
Z represents a nitrogen atom or a C—$R_4$ group,
$R_1$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl group, a cyano group, a nitro group, -$Cy_8$, -alkyl($C_0$-$C_6$)—$NR_{11}R_{11}$', —O-alkyl($C_1$-$C_6$)—$NR_{11}R_{11}$', —O-alkyl($C_1$-$C_6$)—$R_{12}$, —C(O)—$OR_{11}$, —O—C(O)—$R_{11}$, —C(O)—$NR_{11}R_{11}$', —$NR_{11}$—C(O)—$R_{11}$', —$NR_{11}$—C(O)—$OR_{11}$', -alkyl($C_1$-$C_6$)—$NR_{11}$—C(O)—$R_{11}$', —$SO_2$—$NR_{11}R_{11}$', or —$SO_2$-alkyl($C_1$-$C_6$), $R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}$', —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$NR_{11}R_{11}$', —O-alkyl($C_1$-$C_6$)—$R_{12}$, —C(O)—$OR_{11}$, —O—C(O)—$R_{11}$, —C(O)—$NR_{11}R_{11}$', —$NR_{11}$—C(O)—$R_{11}$', —$NR_{11}$—C(O)—$OR_{11}$', -alkyl($C_1$-$C_6$)—$NR_{11}$—C(O)—$R_{11}$', —$SO_2$—$NR_{11}R_{11}$', or —$SO_2$-alkyl($C_1$-$C_6$), or the substituents of the pair ($R_1$, $R_2$), ($R_2$, $R_3$), ($R_3$, $R_4$), ($R_4$, $R_5$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by from 1 to 2 groups selected from halogen, linear or branched ($C_1$-$C_6$)alkyl, -alkyl($C_0$-$C_6$)—$NR_{11}R_{11}$', —$NR_{13}R_{13}$', -alkyl($C_0$-$C_6$)-$Cy_1$ or oxo, $R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}$', —O-alkyl($C_1$-$C_6$)—$NR_{11}R_{11}$', —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}$', —$NR_{11}$—C(O)—$R_{11}$', —$NR_{11}$—C(O)—$OR_{11}$', -alkyl($C_1$-$C_6$)—$NR_{11}$—C(O)—$R_{11}$', —$SO_2$—$NR_{11}R_{11}$', or —$SO_2$-alkyl($C_1$-$C_6$), or the substituents of the pair ($R_6$, $R_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{13}R_{13}$', -alkyl($C_0$-$C_6$)-$Cy_1$ or an oxo, W represents a —$CH_2$— group, a —NH— group or an oxygen atom, $R_8$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group, $R_9$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, -$Cy_2$, -alkyl($C_1$-$C_6$)-$Cy_2$, -alkenyl($C_2$-$C_6$)-$Cy_2$, -alkynyl($C_2$-$C_6$)-$Cy_2$, -$Cy_2$-$Cy_3$, -alkynyl($C_2$-$C_6$)—O-$Cy_2$, -$Cy_2$-alkyl($C_0$-$C_6$)—O-alkyl($C_0$-$C_6$)-$Cy_3$, a halogen atom, a cyano group, —C(O)—$R_{14}$, or —C(O)—$NR_{14}R_{14}$', $R_{10}$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, an arylalkyl($C_1$-$C_6$) group, a cycloalkylalkyl($C_1$-$C_6$) group, a linear or branched ($C_1$-$C_6$)polyhaloalkyl, or -alkyl($C_1$-$C_6$)—O-$Cy_4$, or the substituents of the pair ($R_9$, $R_{10}$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, $R_{11}$ and $R_{11}'$ independently of one another represent a hydrogen atom, an optionally substituted linear or branched ($C_1$-$C_6$)alkyl group, or -alkyl($C_0$-$C_6$)-$Cy_1$, or the substituents of the pair ($R_{11}$, $R_{11}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by from 1 to 2 groups representing a hydrogen atom, or a linear or branched ($C_1$-$C_6$)alkyl group and it being understood that one or more of the carbon atoms of the possible substituents, may be deuterated, $R_{12}$ represents -$Cy_5$, -$Cy_5$-alkyl($C_0$-$C_6$)—O-alkyl($C_0$-$C_6$)-$Cy_6$, -$Cy_5$-alkyl($C_0$-$C_6$)-$Cy_6$, -$Cy_5$-alkyl($C_0$-$C_6$)—$NR_{11}$-alkyl($C_0$-$C_6$)-$Cy_6$, -$Cy_5$-$Cy_6$-O-alkyl($C_0$-$C_6$)-$Cy_7$, -$Cy_5$-alkyl($C_0$-$C_6$)—O-alkyl($C_0$-$C_6$)-$Cy_9$, -$Cy_5$-alkyl($C_0$-$C_6$)-$Cy_9$, —NH—C(O)—NH—$R_{11}$, -$Cy_5$-alkyl($C_0$-$C_6$)—$NR_{11}$-alkyl($C_0$-$C_6$)-$Cy_9$, —C(O)—$NR_{11}R_{11}'$, —$NR_{11}R_{11}'$, —$OR_{11}$,

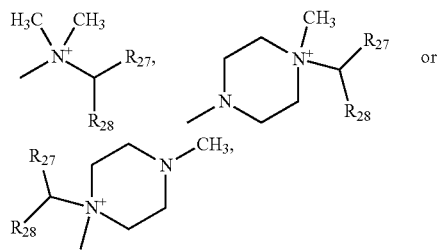

it being possible for the ammonium so defined to exist as a zwitterionic form or to have a monovalent anionic counterion, $R_{13}$, $R_{13}'$, $R_{14}$ and $R_{14}'$ independently of one another represent a hydrogen atom, or an optionally substituted linear or branched ($C_1$-$C_6$)alkyl group, $R_a$ represents a hydrogen atom or a linear or branched ($C_1$-$C_6$)alkyl group, $R_b$ represents a —O—C(O)—O—$R_c$ group, a —O—C(O)—$NR_cR_c'$ group, or a —O—P(O)($OR_c$)$_2$ group, $R_c$ and $R_c'$ independently of one another represent a hydrogen atom, a linear or branched ($C_1$-$C_8$)alkyl group, a cycloalkyl group, a ($C_1$-$C_6$)alkoxy($C_1$-$C_6$) alkyl group, or a ($C_1$-$C_6$)alkoxycarbonyl($C_1$-$C_6$)alkyl group, or the substituents of the pair ($R_c$, $R_c'$) form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched ($C_1$-$C_6$)alkyl group, $Cy_1$, $Cy_2$, $Cy_3$, $Cy_4$, $Cy_5$, $Cy_6$, $Cy_7$, $Cy_8$ and $Cy_{10}$ independently of one another, represent a cycloalkyl group, a heterocycloalkyl group, an aryl group or a heteroaryl group, $Cy_9$ represents

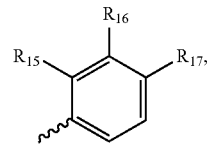

or $Cy_9$ represents a heteroaryl group which is substituted by a group selected from —O—P(O)($OR_{20}$)$_2$; —O—P(O)($O^-M^+$)$_2$; —($CH_2$)$_p$—O—($CHR_{18}$—$CHR_{19}$—O)$_q$—$R_{20}$; hydroxy; hydroxy($C_1$-$C_6$)alkyl; —($CH_2$)$_r$—U—($CH_2$)$_s$-heterocycloalkyl; or —U—($CH_2$)$_q$—$NR_{21}R_{21}'$, $R_{15}$ represents a hydrogen atom; a —($CH_2$)$_p$—O—($CHR_{18}$—$CHR_{19}$—O)$_q$—$R_{20}$ group; a linear or branched ($C_1$-$C_6$)alkoxy($C_1$-$C_6$)alkyl group; a —U—($CH_2$)$_q$—$NR_{21}R_{21}'$ group; or a —($CH_2$)$_r$—U—($CH_2$)$_s$-heterocycloalkyl group, $R_{16}$ represents a hydrogen atom; a hydroxy group; a hydroxy($C_1$-$C_6$)alkyl group;

a —($CH_2$)$_r$—U—($CH_2$)$_s$-heterocycloalkyl group; a —($CH_2$)$_r$—U—V—O—P(O)($OR_{20}$)$_2$ group;

a —O—P(O)($O^-M^+$)$_2$ group; a —($CH_2$)$_p$—O—($CHR_{18}$—$CHR_{19}$—O)$_q$—$R_{20}$ group;

a —($CH_2$)$_p$—O—C(O)—$NR_{22}R_{23}$ group; or a —U—($CH_2$)$_q$—$NR_{21}R_{21}'$ group, $R_{17}$ represents a hydrogen atom; a —($CH_2$)$_p$—O—($CHR_{18}$—$CHR_{19}$—O)$_q$—$R_{20}$ group;

a —O—P(O)($OR_{20}$)$_2$ group; a —O—P(O)($O^-M^+$)$_2$ group; a hydroxy group;

a hydroxy($C_1$-$C_6$)alkyl group; a —($CH_2$)$_r$—U—($CH_2$)$_s$-heterocycloalkyl group;

a —U—($CH_2$)$_q$—$NR_{21}R_{21}'$ group; or an aldonic acid, $M^+$ represents a pharmaceutically acceptable monovalent cation, U represents a bond or an oxygen atom, V represents a —($CH_2$)$_s$— group or a —C(O)— group, $R_{18}$ represents a hydrogen atom or a ($C_1$-$C_6$)alkoxy($C_1$-$C_6$)alkyl group, $R_{19}$ represents a hydrogen atom or a hydroxy($C_1$-$C_6$)alkyl group, $R_{20}$ represents a hydrogen atom or a linear or branched ($C_1$-$C_6$)alkyl group, $R_{21}$ and $R_{21}'$ independently of one another represent a hydrogen atom, a linear or branched ($C_1$-$C_6$)alkyl group, or a hydroxy($C_1$-$C_6$)alkyl group, or the substituents of the pair ($R_{21}$, $R_{21}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the resulting ring may be substituted by a group representing a hydrogen atom or a linear or branched ($C_1$-$C_6$) alkyl group, $R_{22}$ represents a ($C_1$-$C_6$)alkoxy($C_1$-$C_6$)alkyl group, a —($CH_2$)$_p$—$NR_{24}R_{24}'$ group, or a —($CH_2$)$_p$—O—($CHR_{18}$—$CHR_{19}$—O)$_q$—$R_{20}$ group, $R_{23}$ represents a hydrogen atom or a ($C_1$-$C_6$)alkoxy($C_1$-$C_6$)alkyl group, or the substituents of the pair ($R_{22}$, $R_{23}$) form together with the nitrogen atom carrying them an aromatic or non-aromatic ring composed of from 5 to 18 ring members, which may contain in addition to the nitrogen atom from 1 to 5 heteroatoms selected from oxygen, sulphur and nitrogen, it being understood that the resulting ring may be substituted by a group representing a hydrogen atom, a linear or branched ($C_1$-$C_6$)alkyl group or a heterocycloalkyl group, $R_{24}$ and $R_{24}'$ independently of one another represent a hydrogen atom or a linear or branched ($C_1$-$C_6$)alkyl group, or the substituents of the pair ($R_{24}$, $R_{24}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the resulting ring may be substituted by a group representing a hydrogen atom or a linear or branched ($C_1$-$C_6$) alkyl group, $R_{25}$ represents a hydrogen atom, a hydroxy group, or a hydroxy($C_1$-$C_6$)alkyl group, $R_{26}$ represents a hydrogen atom, a halogen atom, a linear or branched ($C_1$-$C_6$)alkyl group, or a cyano group, $R_{27}$ represents a hydrogen atom or a linear or branched ($C_1$-$C_6$)alkyl group, $R_{28}$ represents a —O—P(O)(O⁻)(O⁻) group, a —O—P(O)(O⁻)(OR$_{30}$) group, a —O—P(O)(OR$_{30}$)(OR$_{30}'$) group, a —O—SO$_2$—O⁻ group, a —O—SO$_2$—OR$_{30}$ group, -Cy$_{10}$, a —O—C(O)—R$_{29}$ group, a —O—C(O)—OR$_{29}$ group or a —O—C(O)—NR$_{29}$R$_{29}'$ group;

$R_{29}$ and $R_{29}'$ independently of one another represent a hydrogen atom, a linear or branched ($C_1$-$C_6$)alkyl group or a linear or branched amino($C_1$-$C_6$)alkyl group, $R_{30}$ and $R_{30}'$ independently of one another represent a hydrogen atom, a linear or branched ($C_1$-$C_6$)alkyl group or an arylalkyl($C_1$-$C_6$) group, n is an integer equal to 0 or 1, p is an integer equal to 0, 1 or 2, q is an integer equal to 1, 2, 3 or 4, r and s are independently an integer equal to 0 or 1, it being understood that:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched ($C_1$-$C_6$)alkyl, optionally substituted linear or branched ($C_2$-$C_6$) alkenyl group, optionally substituted linear or branched ($C_2$-$C_6$)alkynyl group, optionally substituted linear or branched ($C_1$-$C_6$)alkoxy, optionally substituted ($C_1$-$C_6$) alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched ($C_1$-$C_6$)polyhaloalkyl, trifluoromethoxy, or halogen, it being understood that R' and R" independently of one another represent a hydrogen atom or an optionally substituted linear or branched ($C_2$-$C_6$)alkyl group, and it being understood that one or more of the carbon atoms of the preceding possible substituents, may be deuterated, or their enantiomers, diastereoisomers, atropisomers, or addition salts thereof with a pharmaceutically acceptable acid or base, and (b) a taxane compound, for simultaneous, sequential or separate use.

Further enumerated embodiments (E) of the invention are described herein. It will be recognized that features specified in each embodiment may be combined with other specified features to provide further embodiments of the present invention.

E2. A combination according to E1, comprising:

(a) a MCL-1 inhibitor of formula (II), a particular case of MCL-1 inhibitor of formula (I):

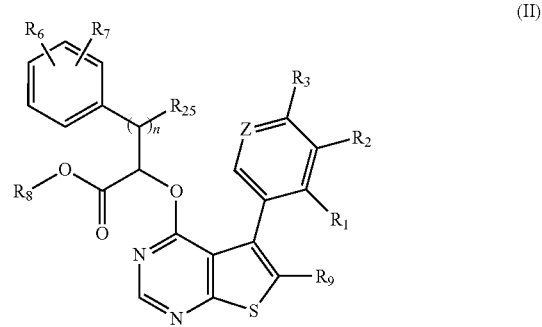

(II)

wherein:

Z represents a nitrogen atom or a C—$R_4$ group, $R_1$ represents a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)alkoxy group, —S—($C_1$-$C_6$)alkyl group, a linear or branched ($C_1$-$C_6$)polyhaloalkyl, a hydroxy group, a cyano, —NR$_{11}$R$_{11}'$, -Cy$_8$ or a halogen atom, $R_2$, $R_3$ and $R_4$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, —S—($C_1$-$C_6$)alkyl group, a cyano group, a nitro group, -alkyl($C_0$-$C_6$)—NR$_{11}$R$_{11}'$, —O-Cy$_1$, -alkyl($C_0$-$C_6$)-Cy$_1$, -alkenyl($C_2$-$C_6$)-Cy$_1$, -alkynyl($C_2$-$C_6$)-Cy$_1$, —O-alkyl($C_1$-$C_6$)—R$_{12}$, —C(O)—OR$_{11}$, —O—C(O)—R$_{11}$, —C(O)—NR$_{11}$R$_{11}'$, —NR$_{11}$—C(O)—R$_{11}'$, —NR$_{11}$—C(O)—OR$_{11}'$, -alkyl($C_1$-$C_6$)—NR$_{11}$—C(O)—R$_{11}'$, —SO$_2$—NR$_{11}$R$_{11}'$, or —SO$_2$-alkyl($C_1$-$C_6$), or the substituents of one of the pairs ($R_2$, $R_3$), ($R_3$, $R_4$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —NR$_{13}$R$_{13}'$, -alkyl($C_0$-$C_6$)-Cy$_1$ or an oxo, $R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$), or the substituents of the pair ($R_6$, $R_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{13}R_{13}'$, -alkyl($C_0$-$C_6$)-$Cy_1$ or an oxo, $R_8$ represents a hydrogen atom, a linear or branched ($C_1$-$C_8$)alkyl group, an aryl group, a heteroaryl group, an arylalkyl($C_1$-$C_6$) group, or a heteroarylalkyl($C_1$-$C_6$) group, $R_9$ represents a linear or branched ($C_1$-$C_6$)alkyl group, a linear or branched ($C_2$-$C_6$)alkenyl group, a linear or branched ($C_2$-$C_6$)alkynyl group, -$Cy_2$, -alkyl($C_1$-$C_6$)-$Cy_2$, -alkenyl($C_2$-$C_6$)-$Cy_2$, -alkynyl($C_2$-$C_6$)-$Cy_2$, -$Cy_2$-$Cy_3$, -alkynyl($C_2$-$C_6$)—O-$Cy_2$, -$Cy_2$-alkyl($C_0$-$C_6$)—O-alkyl($C_0$-$C_6$)-$Cy_3$, a halogen atom, a cyano group, —C(O)—$R_{14}$, or —C(O)—$NR_{14}R_{14}'$, $R_{11}$ and $R_{11}'$ independently of one another represent a hydrogen atom, an optionally substituted linear or branched ($C_1$-$C_6$)alkyl group, or -alkyl($C_0$-$C_6$)-$Cy_1$, or the substituents of the pair ($R_{11}$, $R_{11}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom, or a linear or branched ($C_1$-$C_6$)alkyl group and it being understood that one or more of the carbon atoms of the possible substituents, may be deuterated, $R_{12}$ represents -$Cy_5$, -$Cy_5$-alkyl($C_0$-$C_6$)-$Cy_6$, -$Cy_5$-alkyl($C_0$-$C_6$)—O-alkyl($C_0$-$C_6$)-$Cy_6$, -$Cy_5$-alkyl($C_0$-$C_6$)—$NR_{11}$-alkyl($C_0$-$C_6$)-$Cy_6$, -$Cy_5$-$Cy_6$-O-alkyl($C_0$-$C_6$)-$Cy_7$, —C(O)—$NR_{11}R_{11}'$, —$NR_{11}R_{11}'$, —$OR_{11}$, —$NR_{11}$—C(O)—$R_{11}'$, —O-alkyl($C_1$-$C_6$)—$OR_{11}$, —$SO_2$—$R_{11}$, —C(O)—$OR_{11}$, or —NH—C(O)—NH—$R_{11}$, $R_{13}$, $R_{13}'$, $R_{14}$ and $R_{14}'$ independently of one another represent a hydrogen atom, or an optionally substituted linear or branched ($C_1$-$C_6$)alkyl group, $R_{25}$ represents a hydrogen atom, a hydroxy group, or a hydroxy($C_1$-$C_6$)alkyl group, $Cy_1$, $Cy_2$, $Cy_3$, $Cy_5$, $Cy_6$, $Cy_7$ and $Cy_8$ independently of one another, represent a cycloalkyl group, a heterocycloalkyl group, an aryl group or a heteroaryl group, n is an integer equal to 0 or 1, it being understood that:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched ($C_1$-$C_6$)alkyl, optionally substituted linear or branched ($C_2$-$C_6$) alkenyl group, optionally substituted linear or branched ($C_2$-$C_6$)alkynyl group, optionally substituted linear or branched ($C_1$-$C_6$)alkoxy, optionally substituted ($C_1$-$C_6$) alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched ($C_1$-$C_6$)polyhaloalkyl, trifluoromethoxy, or halogen, it being understood that R' and R" independently of one another represent a hydrogen atom or an optionally substituted linear or branched ($C_1$-$C_6$)alkyl group, and it being understood that one or more of the carbon atoms of the preceding possible substituents, may be deuterated, or their enantiomers, diastereoisomers, atropisomers, or addition salts thereof with a pharmaceutically acceptable acid or base, and (b) a taxane compound, for simultaneous, sequential or separate use.

E3. A combination according to E1 or E2, wherein the taxane compound is paclitaxel or docetaxel.

E4. A combination according to E1 or E2, wherein the MCL-1 inhibitor is (2R)-2-{[(5$S_a$)-5-{3-chloro-2-methyl-4-[2-(4-methylpiperazin-1-yl)ethoxy]phenyl}-6-(5-fluorofuran-2-yl) thieno[2,3-d]pyrimidin-4-yl]oxy}-3-(2-{[1-(2,2,2-trifluoroethyl)-1H-pyrazol-5-yl]methoxy}phenyl) propanoic acid.

E5. A combination according to E1 or E2, wherein the MCL-1 inhibitor is (2R)-2-{[(5$S_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}-3-(2-{[2-(2-methoxyphenyl)pyrimidin-4-yl]methoxy}phenyl)propanoic acid.

E6. A combination according to E1 or E2, wherein the taxane compound is paclitaxel.

E7. A combination according to E1 or E2, wherein the taxane compound is docetaxel.

E8. A combination according to E1 or E2, wherein MCL-1 inhibitor is (2R)-2-{[(5$S_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}-3-(2-{[2-(2-methoxyphenyl)pyrimidin-4-yl]methoxy}phenyl)propanoic acid and the taxane compound is paclitaxel.

E9. A combination according to E1 or E2, wherein MCL-1 inhibitor is (2R)-2-{[(5$S_a$)-5-{3-chloro-2-methyl-4-[2-(4-methylpiperazin-1-yl)ethoxy]phenyl}-6-(5-fluorofuran-2-yl) thieno[2,3-d]pyrimidin-4-yl]oxy}-3-(2-{[1-(2,2,2-trifluoroethyl)-1H-pyrazol-5-yl]methoxy}phenyl) propanoic acid and the taxane compound is paclitaxel.

E10. A combination according to E1 or E2, wherein MCL-1 inhibitor is (2R)-2-{[(5$S_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}-3-(2-{[2-(2-methoxyphenyl)pyrimidin-4-yl]methoxy}phenyl)propanoic acid and the taxane compound is docetaxel.

E11. A combination according to E1 or E2, wherein MCL-1 inhibitor is (2R)-2-{[(5S$_a$)-5-{3-chloro-2-methyl-4-[2-(4-methylpiperazin-1-yl)ethoxy]phenyl}-6-(5-fluoro-furan-2-yl) thieno[2,3-d]pyrimidin-4-yl]oxy}-3-(2-{[1-(2,2,2-trifluoroethyl)-1H-pyrazol-5-yl]methoxy}phenyl) propanoic acid and the taxane compound is docetaxel.

E12. A combination according to E5, wherein the dose of (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid during the combination treatment is from 25 mg to 1500 mg.

E13. A combination according to E5 or E12, wherein (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid is administered during the combination treatment once a week.

E14. A combination according to any of E1 to E13, wherein the MCL-1 inhibitor is administered orally and the taxane compound is administered intravenously.

E15. A combination according to any of E1 to E13, wherein the MCL-1 inhibitor and the taxane compound are administered intravenously.

E16. A combination according to any of E1 to E15, for use in the treatment of cancer.

E17. The combination for use according to E16, wherein the MCL-1 inhibitor and the taxane compound are provided in amounts which are jointly therapeutically effective for the treatment of cancer.

E18. The combination for use according to E16, wherein the MCL-1 inhibitor and the taxane compound are provided in amounts which are synergistically effective for the treatment of cancer.

E19. The combination for use according to E16, wherein the MCL-1 inhibitor and the taxane compound are provided in synergistically effective amounts which enable a reduction of the dose required for each compound in the treatment of cancer, whilst providing an efficacious cancer treatment, with eventually a reduction in side effects.

E20. The combination for use according to any of E16 to E19, wherein the cancer is breast cancer.

E21. The combination for use according to E20, wherein the cancer is triple negative breast cancer, particularly chemoresistant triple negative breast cancer, more particularly, triple negative breast cancer resistant to taxane therapy.

E22. The combination for use according to any of E16 to E19, wherein the cancer is lung cancer, particularly non-small cell lung cancer or small cell lung cancer.

E23. A combination according to any of E1 to E15, further comprising one or more excipients.

E24. Pharmaceutical compositions comprising a combination according to any of E1 to E15, in combination with one or more pharmaceutically acceptable excipients.

E25. Pharmaceutical compositions according to E24, for use in the treatment of cancer.

E26. Pharmaceutical compositions for use according to E25, wherein the cancer is breast cancer.

E27. Pharmaceutical compositions for use according to E26, wherein the cancer is triple negative breast cancer, particularly chemoresistant triple negative breast cancer, more particularly, triple negative breast cancer resistant to taxane therapy.

E28. Pharmaceutical compositions for use according to E25, wherein the cancer is lung cancer, particularly non-small cell lung cancer or small cell lung cancer.

E29. The use of a combination according to any of E1 to E15, in the manufacture of a medicament for the treatment of cancer.

E30. The use according to E29, wherein the cancer is breast cancer.

E31. The use according to E30, wherein the cancer is triple negative breast cancer, particularly chemoresistant triple negative breast cancer, more particularly, triple negative breast cancer resistant to taxane therapy.

E32. The use according to E29, wherein the cancer is lung cancer, particularly non-small cell lung cancer or small cell lung cancer.

E33. A medicament containing, separately or together,
(a) a MCL-1 inhibitor of formula (I) as defined in E1, and
(b) a taxane compound,
for simultaneous, sequential or separate administration, and wherein the MCL-1 inhibitor and the taxane compound are provided in effective amounts for the treatment of cancer.

E34. A medicament containing, separately or together,
(a) a MCL-1 inhibitor of formula (II) as defined in E2, and
(b) a taxane compound,
for simultaneous, sequential or separate administration, and wherein the MCL-1 inhibitor and the taxane compound are provided in effective amounts for the treatment of cancer.

E35. A method of treating cancer, comprising administering a jointly therapeutically effective amount of:
(a) a MCL-1 inhibitor of formula (I) as defined in E1, and
(b) a taxane compound,
to a subject in need thereof.

E36. A method of treating cancer, comprising administering a jointly therapeutically effective amount of:
(a) a MCL-1 inhibitor of formula (II) as defined in E2, and
(b) a taxane compound,
to a subject in need thereof.

E37. A method for sensitizing a patient who is (i) refractory to at least one chemotherapy treatment, or (ii) in relapse after treatment with chemotherapy, or both (i) and (ii), wherein the method comprises administering a jointly therapeutically effective amount of MCL-1 inhibitor of formula (I) as defined in E1 in combination with a taxane compound as described herein, to said patient.

E38. A method for sensitizing a patient who is (i) refractory to at least one chemotherapy treatment, or (ii) in relapse after treatment with chemotherapy, or both (i) and (ii), wherein the method comprises administering a jointly therapeutically effective amount of MCL-1 inhibitor of formula (II) as defined in E2 in combination with a taxane compound as described herein, to said patient.

'Combination' refers to either a fixed dose combination in one unit dosage form (e.g., capsule, tablet, or sachet), non-fixed dose combination, or a kit of parts for the combined administration where a compound of the present invention and one or more combination partners (e.g. another drug as explained below, also referred to as 'therapeutic agent' or 'co-agent') may be administered independently at the same time or separately within time intervals, especially where these time intervals allow that the combination partners show a cooperative, e.g. synergistic effect.

The terms 'co-administration' or 'combined administration' or the like as utilized herein are meant to encompass administration of the selected combination partner to a single subject in need thereof (e.g. a patient), and are intended to include treatment regimens in which the agents are not necessarily administered by the same route of administration or at the same time.

The term 'fixed dose combination' means that the active ingredients, e.g. a compound of formula (I) and one or more combination partners, are both administered to a patient simultaneously in the form of a single entity or dosage.

The term 'non-fixed dose combination' means that the active ingredients, e.g. a compound of the present invention and one or more combination partners, are both administered to a patient as separate entities either simultaneously or sequentially, with no specific time limits, wherein such administration provides therapeutically effective levels of the two compounds in the body of the patient. The latter also applies to cocktail therapy, e.g. the administration of three or more active ingredients.

'Cancer' means a class of disease in which a group of cells display uncontrolled growth. Cancer types include solid tumors including carcinoma, sarcoma, or blastoma. In particular 'cancer' refers to breast and lung cancer.

The term 'jointly therapeutically effective' means that the therapeutic agents may be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both compounds are present in the blood of the human to be treated at least during certain time intervals.

'Synergistically effective' or 'synergy' means that the therapeutic effect observed following administration of two or more agents is greater than the sum of the therapeutic effects observed following the administration of each single agent.

As used herein, the term 'treat', 'treating' or 'treatment' of any disease or disorder refers in one embodiment, to ameliorating the disease or disorder (i.e., slowing or arresting or reducing the development of the disease or at least one of the clinical symptoms thereof). In another embodiment 'treat', 'treating' or 'treatment' refers to alleviating or ameliorating at least one physical parameter including those which may not be discernible by the patient. In yet another embodiment, 'treat', 'treating' or 'treatment' refers to modulating the disease or disorder, either physically, (e.g., stabilization of a discernible symptom), physiologically, (e.g., stabilization of a physical parameter), or both.

As used herein, a subject is 'in need of' a treatment if such subject would benefit biologically, medically or in quality of life from such treatment.

In another aspect, provided is a method for sensitizing a human who is (i) refractory to at least one chemotherapy treatment, or (ii) in relapse after treatment with chemotherapy, or both (i) and (ii), wherein the method comprises administering a MCL-1 inhibitor of formula (I) or formula (II) in combination with a taxane compound, as described herein, to the patient. A patient who is sensitized is a patient who is responsive to the treatment involving administration of a MCL-1 inhibitor of formula (I) or formula (II) in combination with a taxane compound, as described herein, or who has not developed resistance to such treatment.

'Medicament' means a pharmaceutical composition, or a combination of several pharmaceutical compositions, which contains one or more active ingredients in the presence of one or more excipients.

In the pharmaceutical compositions according to the invention, the proportion of active ingredients by weight (weight of active ingredients over the total weight of the composition) is from 5 to 50%.

Among the pharmaceutical compositions according to the invention there will be more especially used those which are suitable for administration by the oral, parenteral and especially intravenous, per- or trans-cutaneous, nasal, rectal, perlingual, ocular or respiratory route, more specifically tablets, dragées, sublingual tablets, hard gelatin capsules, glossettes, capsules, lozenges, injectable preparations, aerosols, eye or nose drops, suppositories, creams, ointments, dermal gels etc.

The pharmaceutical compositions according to the invention comprise one or more pharmaceutically acceptable excipients or carriers selected from diluents, lubricants, binders, disintegration agents, stabilizers, preservatives, absorbents, colorants, sweeteners, flavorings etc.

By way of non-limiting example there may be mentioned:
- as diluents: lactose, dextrose, sucrose, mannitol, sorbitol, cellulose, glycerol,
- as lubricants: silica, talc, stearic acid and its magnesium and calcium salts, polyethylene glycol,
- as binders: magnesium aluminium silicate, starch, gelatin, tragacanth, methylcellulose, sodium carboxymethylcellulose and polyvinylpyrrolidone,
- as disintegrants: agar, alginic acid and its sodium salt, effervescent mixtures.

The compounds of the combination may be administered simultaneously or sequentially. The administration route is preferably the intravenous infusion or injection, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

The useful dosage regimen varies according to the sex, age and weight of the patient, the administration route, the nature of the cancer and of any associated treatments and ranges from 25 mg to 1500 mg of MCL-1 inhibitor per week, more preferably from 50 mg to 1400 mg per week. The dose of the taxane compound will be the same as that used when it is administered on its own.

Pharmacological Data

Example 1: In Vitro Effect on Proliferation of Combining MCL-1 Inhibitor (Compound 1) with Paclitaxel in Breast and Lung Cancer Cell Lines The effect on proliferation of combining MCL-1 inhibitor (Compound 1) with paclitaxel was assessed in a panel of 19 breast cancer cell lines (BT-20, BT-474, BT-549, Cal-148, HCC1143, HCC1395, HCC1500, HCC1937, HCC1954, HCC38, HCC70, Hs 578T, MCF7, MDA-MB-157, MDA-MB-231, MDA-MB-436, MDA-MB-453, MDA-MB-468 and SK-BR-3) and 3 lung cancer cell line (H522, H23 and A549).

Material and Method

Compounds were dissolved in 100% DMSO (Sigma, Catalog # D2438-50 ML) at a stock concentration of 10 mM and stored at −20° C. until use. Compounds were arrayed in 2 ml deep 96-well plates (Greiner bio-one, catalog number 780271) serially diluted 3-fold. Compound 1 was used over a concentration range of 0.0-10.0 µM. Paclitaxel was used over a concentration range of 0.0-1.0 µM in breast cancer cells and 0.0-2.0 µM range in lung cancer cells.

All cell lines were purchased from the American Type Culture Collection and cultured according to vendor recommendations. All lines were supplemented with 10% FBS (GIBCO, Catalog number 10099-141). All cell lines were determined to be free of mycoplasma contamination by a PCR detection assay performed at Idexx Radil (Columbia, Mo., USA) and authenticated by SNP analysis. Cells were thawed from frozen stocks, expanded through ≥1 passage and grown at 37° C. in 5% $CO_2$. Cells were expanded to T-75 flasks and assessed for viability using a Beckman-Coulter ViCell counter prior to plating. To split and expand cell lines, cells were dislodged from flasks using 0.25% Trypsin-EDTA (Corning Costar, Catalog #25-053-CL).

Cell proliferation was measured in 72 hours CellTiter-Glo™ (CTG) assays and all results shown are the result of at least triplicate measurements. The cells were dispensed into tissue culture treated 96-well plates (Costar, catalog number 3904) with a final volume of 80 µL of medium and at density of 3000 cells per well. 16 to 24 hours after plating, 20 µL of each compound dilution series were transferred to plates containing the cells, resulting in compound concentration ranges stated above and a final DMSO concentration of 0.16%. Additionally a day zero plate was assayed at this time using the CellTiter-Glo® Luminescent Cell Viability Assay, as described below. After 72 hours of compound treatment the effects of compounds on cell proliferation was determined using the CellTiter-Glo™ Luminescent Cell Viability Assay (Promega, Catalog # G7573). This is a homogeneous method to determine the number of viable cells in culture based on quantitation of the ATP present, which signals the presence of metabolically active cells. The method is described in detail in the Technical Bulletin, TB288 Promega. Briefly, 100 µl of CTG Reagent was added to plates and plates were incubated for 20-30 minutes on an orbital shaker. Plates were then read on the Perkin Elmer Victor™ X4 plate reader.

The percent growth inhibition, excess inhibition and growth inhibition were calculated using Combo Module software using the Loewe synergy model (as described in Lehar et al., *Nature Biotechnology* 2009, 27(7), 659-66), which measures the effect on growth above what would be expected if two drugs behaved in a dose additive manner. Positive numbers represent areas of increasing synergy. The percentage of growth inhibition relative to DMSO is displayed in the panel labelled "Inhibition". The amount of inhibition in excess of the expected amount is in the panel labelled "Loewe Excess Inhibition". The amount of inhibition normalized to day zero is displayed in the panel labelled "Growth Inhibition". Concentrations of Compound 1 are shown along the bottom row from left to right and increasing concentrations of paclitaxel along the left most column from bottom to top. All remaining points in the grids display results from a combination of the two inhibitors that correspond to the single agent concentrations denoted on the two axes. Absolute $IC_{50}$ was determined by finding the compound concentration where the calculated curve crosses the 50% activity mark. Absolute $IC_{50}$ and synergy score were calculated in Combo module software as described in Lehar et al. 2009.

Synergy Score

SS~0→Dose Additive

SS>2→Synergy

SS>1→Weak Synergy

TABLE 1

Single agent absolute $IC_{50}$ values for each compound and synergy score measurements for the combination of Compound 1 and paclitaxel are indicated. Interactions were deemed synergistic when scores ≥2.0 were observed.

| Cell Line | Linage | Compound 1 Abs $IC_{50}$ (nM) | Paclitaxel Abs $IC_{50}$ (nM) | Combination Synergy Score (SS) |
|---|---|---|---|---|
| BT-20 | Breast | 653 | 5.97 | 7.93 |
| BT-474 | Breast | 1262.5 | 1.7 | 4.7 |
| BT-549 | Breast | >10000 | 8.82 | 9.01 |
| Cal-148 | Breast | 1330 | 4.25 | 13.8 |
| HCC1143 | Breast | >10000 | 9.43 | 2.58 |
| HCC1395 | Breast | 9915 | 8.03 | 1.52 |
| HCC1500 | Breast | 257.5 | >1000 | 6.38 |
| HCC1937 | Breast | 137 | 11.6 | 9.4 |
| HCC1954 | Breast | 158.5 | 6.5 | 3.69 |
| HCC38 | Breast | 3385 | 4.33 | 5.19 |
| HCC70 | Breast | 704 | 8.39 | 11.9 |
| Hs 578T | Breast | 519.5 | 0.363 | 8.49 |
| MCF7 | Breast | 1292.5 | 10.4 | 3.82 |
| MDA-MB-157 | Breast | >10000 | >1000 | 0.389 |
| MDA-MB-231 | Breast | >10000 | 17.5 | 4.86 |
| MDA-MB-436 | Breast | >10000 | 14.7 | 1.41 |
| MDA-MB-453 | Breast | >10000 | 4.2 | 23.9 |
| MDA-MB-468 | Breast | 9917.5 | 3.07 | 11.3 |
| SK-BR-3 | Breast | 301 | 2.66 | 4.52 |
| NCI-H522 | Lung | 713 | 0.48 | 14.9 |
| NCI-H23 | Lung | 160 | 0.22 | 6.97 |
| A549 | Lung | >10000 | 0.163 | 4.82 |

Results

Compound 1 as single agent inhibit the growth of 7/19 breast cancer cell lines and 2/3 lung cancer cell lines, with $IC_{50}$ below 1000 nM (Table 1).

Paclitaxel as single agent inhibited the growth of the 17/19 breast cancer cell lines and 3/3 lung cancer cell lines, with $IC_{50}$ below 1000 nM.

Figure 2:
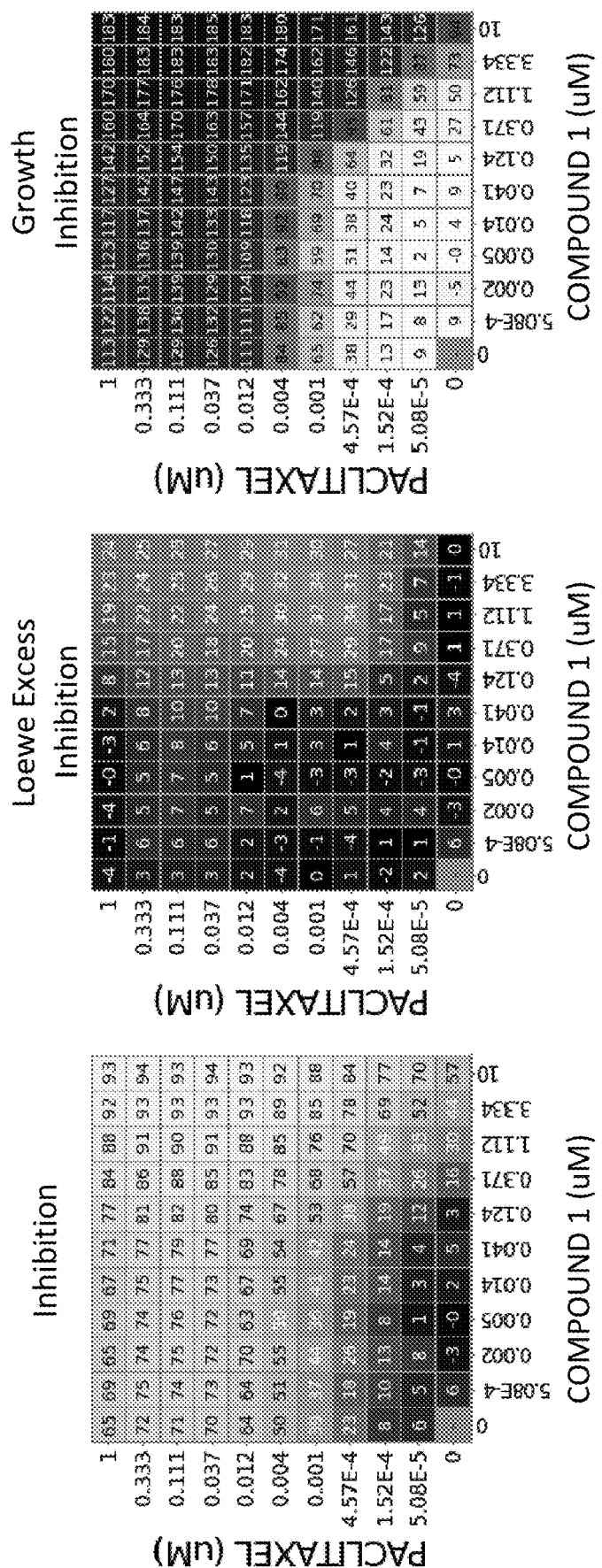
FIG. 2 illustrates matrices for inhibition, Loewe excess inhibition and growth inhibition for paclitaxel combinations with Compound 1 in representative MDA-MB-468 breast cancer cell line.
Figure 3:
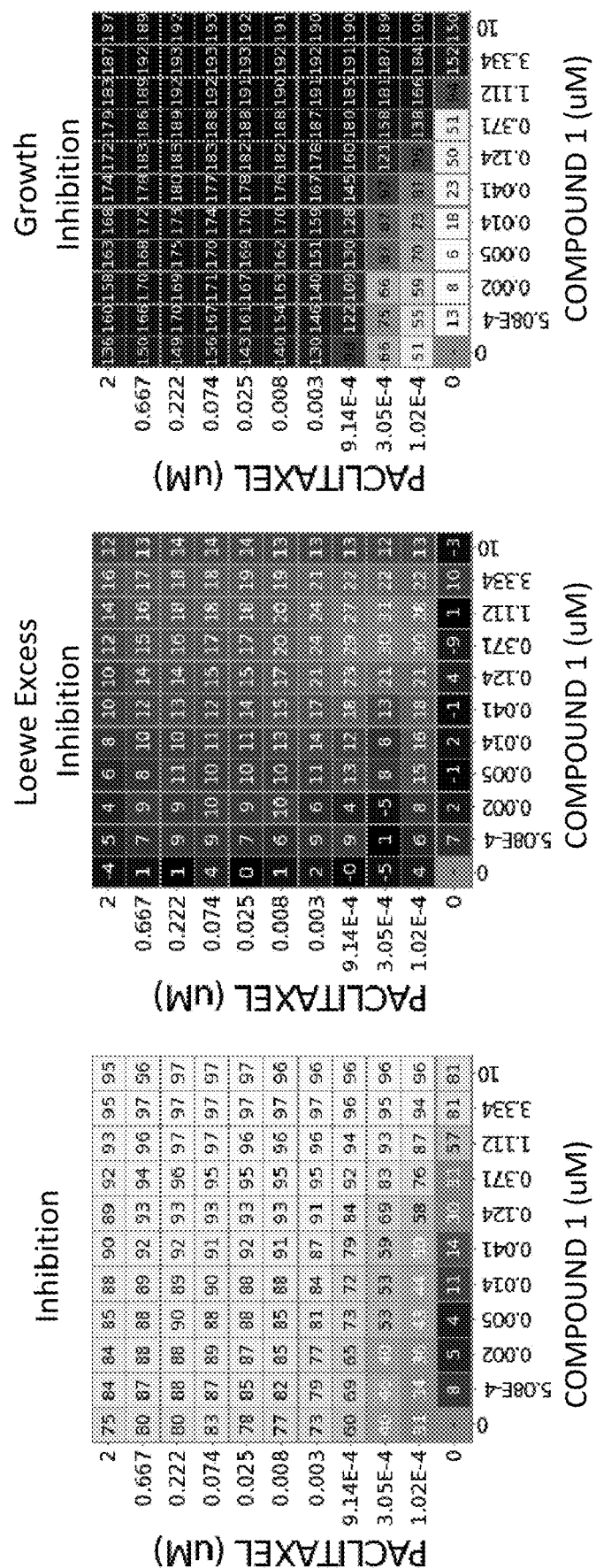
FIG. 3 illustrates matrices for inhibition, Loewe excess inhibition and growth inhibition for paclitaxel combinations with Compound 1 in representative H522 lung cancer cell line.

In combination, Compound 1 and paclitaxel treatment caused synergistic growth inhibition (i.e. Synergy Scores above 2 (Lehar et al, 2009)) in 16/19 breast cancer cell lines and 3/3 lung cancer cell lines (Table 1). In 11 cell lines, the synergy effect was marked, with synergy scores above 6. Importantly, the synergy was not dependent on single agent anti-proliferative effects, and the synergistic effects occurred across a broad range of single agent concentrations (FIGS. 1, 2 and 3), which should prove beneficial in vivo with respect to flexibility concerning dosing levels and scheduling.

Example 2: In Vitro Effect on Proliferation of Combining MCL-1 Inhibitor (Compound 2) with Paclitaxel in Breast and Lung Cancer Cell Lines The effect on proliferation of combining MCL-1 inhibitor (Compound 2) with paclitaxel was assessed in a panel of 2 breast cancer cell lines (MDA-MB-453 and MDA-MB-468) and one lung cancer cell line (H522).

Material and Method

Cell lines were sourced and maintained in the basic media supplemented with fetal bovine serum as indicated in Table 2. In addition, all media contained penicillin (100 IU/ml), streptomycin (100 µg/ml) and L-glutamine (2 mM).

Cell lines were cultured at 37° C. in a humidified atmosphere containing 5% $CO_2$ and expanded in T-150 flasks. In all cases cells were thawed from frozen stocks, expanded through ≥1 passage using appropriate dilutions, counted and assessed for viability using a CASY cell counter prior to plating 150 µl/well at the densities indicated in Table 2 into 96-well plates. All cell lines were determined to be free of mycoplasma contamination in-house.

Stock solutions of compounds were prepared at a concentration of 5 mM in DMSO and stored at −20° C.

Figure 5:
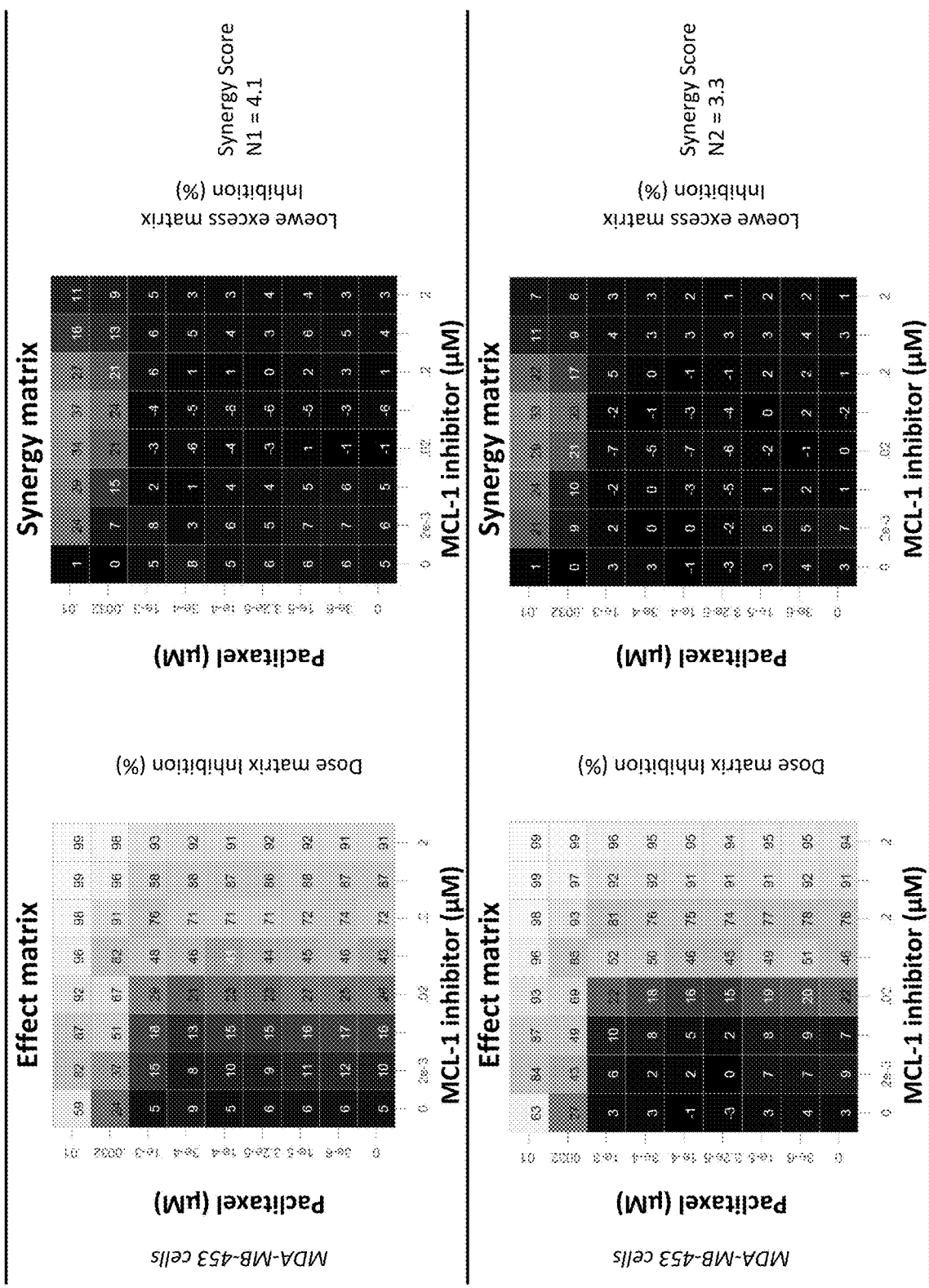
FIG. 5 illustrates exemplary cell growth inhibition effect and synergy combination matrices for inhibition of cell growth (left) and Loewe excess inhibition (right) afforded by Compound 2 in combination with paclitaxel in the lung cancer cell line H522 in two independent experiments. Values in the effect matrix range from 0 (no inhibition) to 100 (total inhibition). Values in the synergy matrix represent the extent of growth inhibition in excess of the theoretical additivity calculated based on the single agent activities of Compound 2 and Paclitaxel at the concentrations tested.
Figure 6:
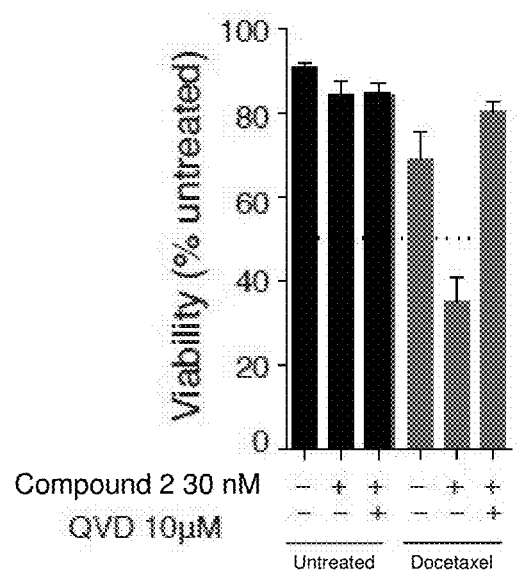
FIG. 6 illustrates synergistic effect of Compound 2 with docetaxel. SK-BR-3 cells were treated with docetaxel (2 nM), or left untreated in the presence of Compound 2 (30 nM), with or without QVD (10 µM) for 72 hours before viability analysis with propidium iodide (PI) staining. Results are presented as a percent of untreated cells and represent 3-5 independent experiments.

In order to analyze the activity of the compounds in single agent or in combination, cells were seeded and treated with seven or eight 3.16-fold serial dilutions of each compound dispensed, either individually or in all possible permutations in a checkerboard fashion, directly into the cell assay plates as indicated in FIGS. 5 and 6. Effects of the single agents as well as their checkerboard combinations on cell viability were assessed after 3 days of incubation at 37° C./5% $CO_2$ by quantification of cellular ATP levels using CellTiterGlo at 75 µL reagent/well. At least two independent experiments, each one performed in duplicates, were performed. Luminescence was quantified on a multipurpose plate reader.

Single agent $IC_{50}$s were calculated using standard four-parametric curve fitting. Potential synergistic interactions between compound combinations were assessed using the Excess Inhibition 2D matrix according to the Loewe additivity model and are reported as Synergy Score (Lehar et al. 2009). All calculations were performed using Clalice™ Bioinformatics Software available in Horizon website.

The doubling time indicated in Table 2 is the mean of the doubling time obtained in the different passages (in T-150 flasks) performed from the thawing of the cells to their seeding in the 96-weel plates.

Synergy Score

SS~0→Additive

SS>1→Weak Synergy

SS>2→Synergy

TABLE 2

Identity and assay conditions for the cell lines used in the combination experiments.

| Cell line | Linage | Medium | % FBS | Source | Doubling time (hours) | Cell number seeded/well |
|---|---|---|---|---|---|---|
| MDA-MB-453 | Breast | L-15 | 10 | ATCC | 41.4 | 15000 |
| MDA-MB-468 | Breast | L-15 | 20 | ATCC | 34.3 | 30000 |
| H522 | Lung | RPMI | 10 | ATCC | 67.2 | 30000 |

TABLE 3

Single agent $IC_{50}$ values for Compound 2 and paclitaxel are indicated. Compounds were incubated with the cells during 3 days.

| | Compound 2 | | Paclitaxel | |
|---|---|---|---|---|
| Cell Line | Start conc [µM] | $IC_{50}$ [µM] | Start conc [µM] | $IC_{50}$ [µM] |
| MDA-MB-453 | 2.00 | >2 | 1.0 | >1 |
| MDA-MB-468 | 2.00 | >2 | 1.0 | 0.0009 |
| H522 | 2.00 | 0.140 | 0.01 | 0.0002 |

TABLE 4

Synergy scores for Compound 2 and paclitaxel combination are indicated. Interactions were deemed synergistic when scores ≥2.0 where observed. Start concentrations of compounds, mean of max inhibition and the standard deviation (sd) of the synergy scores are indicated. Compounds were incubated with the cells during 3 days.

| | Compound 2 | | Paclitaxel | | Combination | |
|---|---|---|---|---|---|---|
| Cell Line | Start conc [µM] | Mean of Max Inh [%] | Start conc [µM] | Mean of Max Inh [%] | Mean of Synergy Score (SS) | Synergy Score Error (sd) |
| MDA-MB-453 | 2.0 | 21.0 | 1.00 | 37.0 | 16.9 | 0.5 |
| MDA-MB-468 | 2.0 | 24.0 | 1.00 | 75.0 | 6.5 | 0.2 |
| H522 | 2.0 | 92.0 | 0.01 | 61.0 | 3.7 | 0.6 |

Results

Compound 2 as single agent inhibited the growth of 1/3 cell lines tested, with $IC_{50}$ of 140 nM for H522 cell line (Table 3).

Paclitaxel as single agent inhibited the growth of the 2/3 lines tested, with $IC_{50}$ below 1 nM.

Figure 4:
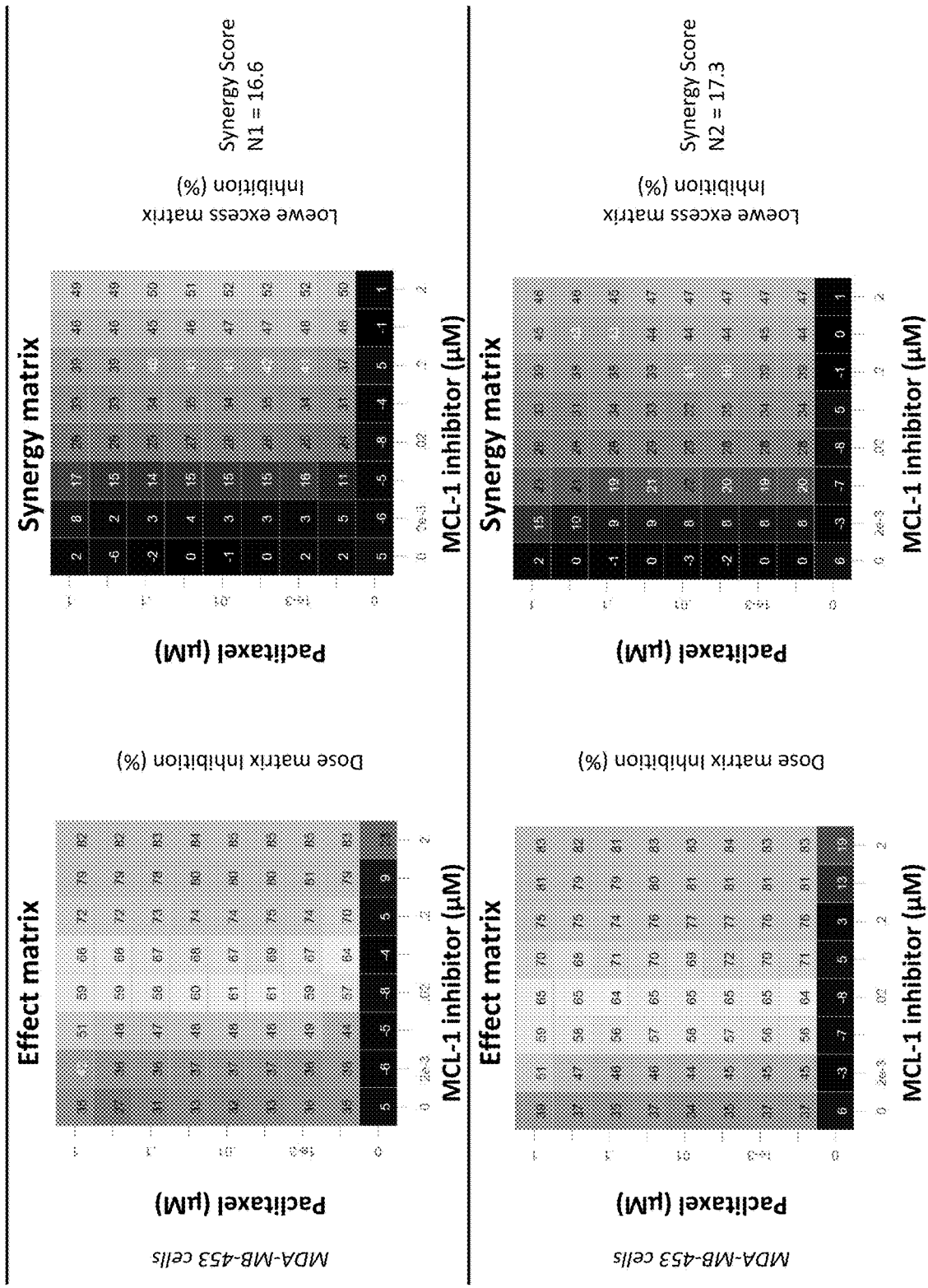
FIG. 4 illustrates exemplary cell growth inhibition effect and synergy combination matrices for inhibition of cell growth (left) and Loewe excess inhibition (right) afforded by Compound 2 in combination with paclitaxel in the breast cancer cell line MDA-MB-453 in two independent experiments. Values in the effect matrix range from 0 (no inhibition) to 100 (total inhibition). Values in the synergy matrix represent the extent of growth inhibition in excess of the theoretical additivity calculated based on the single agent activities of Compound 2 and paclitaxel at the concentrations tested.

In combination, Compound 2 and paclitaxel treatment caused synergistic growth inhibition (i.e. Synergy Scores above 2 (Lehar et al. 2009)) in the three cell lines tested (Table 4). In 2 cell lines, the synergy effect was marked, with synergy scores of 6.5 and 16.9. Importantly, the synergy was not dependent on single agent anti-proliferative effects, and the synergistic effects occurred across a broad range of single agent concentrations (FIGS. 4 and 5), which should prove beneficial in vivo with respect to flexibility concerning dosing levels and scheduling.

Example 3: Synergy Between MCL-1 Inhibitor and Docetaxel In Vitro

We investigated whether MCL-1 inhibitor (Compound 2) elicited synergistic activity with agents currently used in the treatment of TNBC. Compound 2 was combined with docetaxel in SK-BR-3 cells.

Material and Method

Cell Lines: The breast cancer cell line SK-BR-3 was maintained in RPMI-1640 plus GlutaMAX-1 (Gibco) supplemented with 10% fetal calf serum (FCS) and 10 µg/ml insulin. For viability assays, cells were plated at 2×10$^5$ cells/ml in 96 well plates, in RPMI-1640 medium (Gibco) supplemented with 10% FCS and 10 µg/ml insulin, and treated with increasing concentrations of Compound 2.

Cell Viability: Cell viability was assessed using the Cell Titer Glo Luminescent Assay (Promega) as per the manufacturer's instructions. The broad-spectrum caspase inhibitor QVD-OPh hydrate (Sigma-Aldrich) was used at 10 µM. Propidium iodide exclusion (5 µg/ml) was analyzed by flow cytometry. For in vitro cell assays to address synergy between different drugs, combination effects were determined using the Bliss independence method (Prichard et al., *Antimicrobial Agents and Chemotherapy* 1991, 35, 1060-5).

Results

Figure 7:
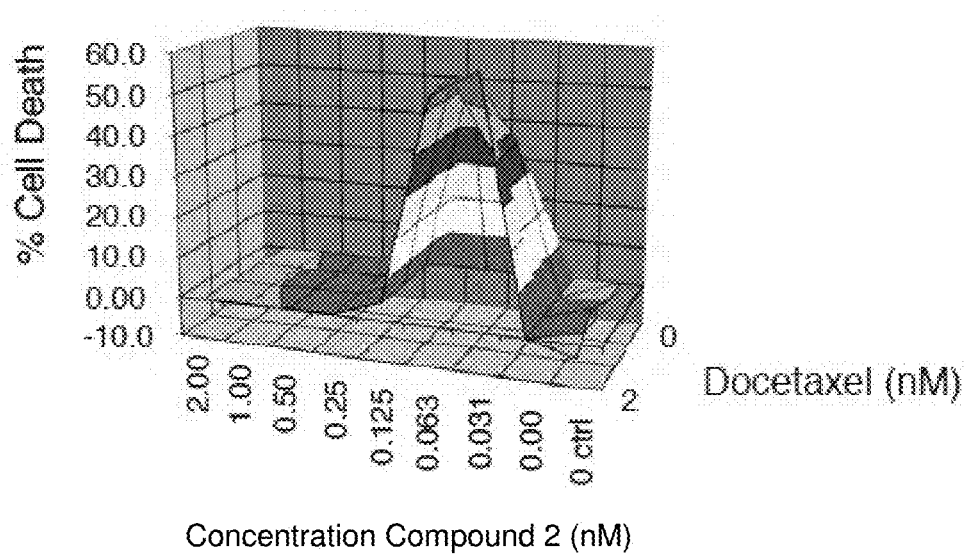
FIG. 7 illustrates synergistic effect of Compound 2 with docetaxel. SK-BR-3 cells were treated with increasing concentrations of Compound 2 and docetaxel for 72 hours, then subjected to viability assays using Cell Titer Glo followed by BLISS score analysis. BLISS synergy values are >0.0 on vertical axis.

Docetaxel and MCL-1 inhibitors showed marked synergy at very low concentrations of both components. Particularly, docetaxel and Compound 2 showed marked synergy at very low concentrations of docetaxel (2 nM) and Compound 2 (31 nM) (FIGS. 6 and 7). Inhibition of caspases with the pan-caspase inhibitor QVD-OPH efficiently blocked cell death, confirming that cell death was triggered via apoptosis (FIG. 6).

Example 4: MCL-1 Inhibition Sensitizes PDX Tumors to Taxane Treatment In Vivo

Since in vitro assays revealed that breast cancer cell lines were sensitive to Compound 2 in combination therapy, we next determined their therapeutic effect in vivo in three PDX models, representing three TNBCs (110T, 838T and PDX OD-BRE-0589).

Material and Method

Human breast cancer tissues were obtained from consenting patients through the Royal Melbourne Hospital Tissue Bank, the Victorian Cancer Biobank and Georges-Francois Leclerc Center with relevant institutional review board approval. Human Ethics approval was obtained from the Walter and Eliza Hall Institute (WEHI) Human Research Ethics Committee and from the Georges-Francois Leclerc Center Human Research Ethics Committee. NOD SCID IL2 gamma receptor knockout mice or SCID mice were bred and maintained according to institutional guidelines. All animal experiments were approved by the WEHI and Servier Research Institute (IdRS) Animal Ethics Committee.

Compound 2 (25 mg/kg) or its vehicle was injected i.v. weekly for six weeks. Compound 2 was dissolved in 20% (2-hydroxypropyl)-β-cyclodextrin and 25 mM hydrochloric acid. Docetaxel (10 mg/kg i.p.) or its vehicle was prepared as previously described (Oakes et al., *Proceedings of the National Academy of Sciences of the USA* 2012, 109, 2766-71) and injected i.p. weekly one day prior to Compound 2. Mice were monitored for tumor development three times weekly and tumor size measured using electronic vernier calipers. Tumor volume was estimated by measuring the minimum and maximum tumor diameters using the formula: (minimum diameter)$^2$(maximum diameter)/2. Once tumors arose, mice were randomized into treatment arms. Treatment was initiated when the tumor volume reached 80-120 mm$^3$. Randomization and tumor measurements were managed using the Study Director software (v 3.0, studylog). Mice were sacrificed at the first measurement for which tumor volume exceeded 600 mm$^3$ or animal health deterioration that are not due to disease progression or drug toxicity (mice censored).

Results

Compound 2 alone was insufficient in inhibiting tumor growth. However, we observed a superior activity in combination with docetaxel as compared to docetaxel administered as a single agent, resulting in significantly improved animal survival in the three PDX models (FIG. 8).

These results indicate that MCL-1 inhibitors combined with taxane compounds are likely to significantly enhance tumor response and clinical outcome.

Example 5: MCL-1 Inhibitor Combined with Docetaxel is Well Tolerated In Vivo

Figure 9:
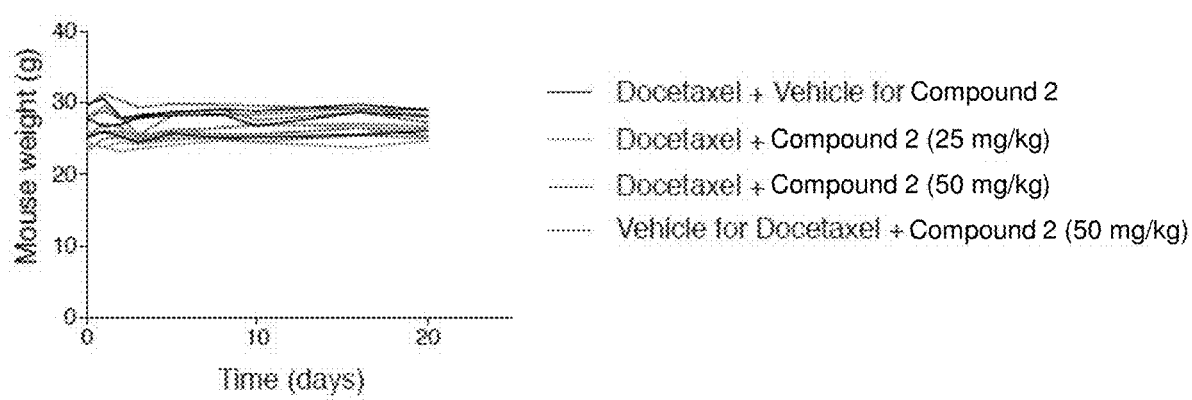
FIG. 9 illustrates the maintaining of normal body weight during therapy. NOD SCID IL2 gamma receptor knockout mice were treated with docetaxel (15 mg/kg, once i.p.) and Compound 2 at 25 or 50 mg/kg (3 mice per group, i.v. injections, once per week for 3 weeks). Their body weight was monitored three times per week for 3 weeks. Compound 2 therapy as single agent or combined with docetaxel was well tolerated.

NOD SCID IL2 gamma receptor knockout mice were treated with docetaxel (15 mg/kg, once i.p.) and Compound 2 at 25 or 50 mg/kg (3 mice per group, i.v. injections, once per week for 3 weeks). Their body weight was monitored three times per week for 3 weeks. Compound 2 combined with docetaxel was well-tolerated and did not induce significant body weight loss (FIG. 9).

Example 6: Efficacy of Compound 1 in Combination with Paclitaxel in MDA-MB-231 Breast Xenograft Model in Nude Rats Methods This study evaluated the antitumor activity and tolerability of Compound 1 in combination with paclitaxel in the triple negative breast cancer (TNBC) model, MDA-MB-231, in female NTac:NIH-Whn nude rats (Taconic).

Compound 1 (free base) and paclitaxel (Sandoz) was used in these studies. Paclitaxel was diluted as per manufacturer's instruction with sterile 5% (w/v) glucose solution to 1.5 mg/ml to administer 7.5 mg/kg in 5 ml/kg dose volume [final ethanol and Cremophor EL concentration was 10 and 15%, respectively in 5% (w/v) glucose solution]. Compound 1 was formulated in a liposomal formulation (Novartis) at 5 mg/ml to administer 50 mg/kg dose in 10 ml/kg dose volume.

MDA-MB-231, a triple negative breast cancer cell line, was obtained from ATCC cell bank. The cells were cultured at 37° C. in an atmosphere of 5% $CO_2$ in air in DMEM high glucose medium (BioConcept Ltd. Amimed) supplemented with 10% FCS (BioConcept Ltd. Amimed, #2-01F36-I) and 4 mM L-glutamine (BioConcept Ltd. Amimed, #5-10K00-H). To establish MDA-MB-231 xenografts cells were harvested and re-suspended in HBSS (Gibco, #14175) and mixed with Matrigel (BD Bioscience, #354234) (1:1 v/v) before injecting 200 L containing 1×10$^7$ cells subcutaneously in the right flanks of animals which were anesthetized with isoflurane. Twenty four hours prior to cell inoculation all animals were irradiated with 5 Gy over 2 minutes using a γ-irradiator. Tumor growth was monitored regularly post cell inoculation and animals were randomised into treatment groups (n=7-8) with a mean tumor volume of about 400 mm$^3$. Groups were treated with:
1) the vehicle used for formulating paclitaxel, iv plus liposomal vehicle iv; or
2) 7.5 mg/kg iv bolus paclitaxel plus liposomal vehicle iv; or
3) the vehicle used for formulating paclitaxel iv plus Compound 1 at 50 mg/kg iv; or
4) 7.5 mg/kg iv paclitaxel plus 50 mg/k iv Compound 1.

The vehicle for paclitaxel or paclitaxel was administered once a week (QW) as a slow bolus dose via a caudal vein 0.5 h or 16 h before the vehicle for Compound 1 or Compound 1 itself in liposomal formulation and these were administered by iv infusion over 15 minutes in a caudal vein. For bolus administrations and 15 minute infusions animals were anesthetized for about 5 and 25 minutes, respectively with isoflurane/$O_2$. Tumor volumes were measured using calipers 2-3 times per week. Tumor size, in mm$^3$, was calculated from: (L×W$^2$×π/6), where W=width and L=length of the tumor. Animals were also weighed 2-3 times per week and examined frequently for overt signs of any adverse effects.

Tumor and body weight change data were analyzed statistically using GraphPad Prism 7.00 (GraphPad Software). If the variances in the data were normally distributed, the data were analyzed using one-way ANOVA with post hoc Dunnett's test for comparison of treatment versus control group. The post hoc Tukey's test was used for intragroup comparison. Otherwise, the Kruskal-Wallis ranked test post hoc Dunn's was used. When applicable, results are presented as mean±SEM.

As a measure of efficacy the % T/C value is calculated at the end of the experiment according to:

(Δtumor volume$^{treated}$/Δtumor volume$^{control}$)*100

Tumor regression was calculated according to:

−(Δtumor volume$^{treated}$/tumor volume$^{treated\ at\ start}$)
*100 where Δtumor volumes represent the mean tumor volume on the evaluation day minus the mean tumor volume at the start of the experiment.

Results: Efficacy and Tolerability

Compound 1 50 mg/kg dosed 0.5 h or 16 h after vehicle for paclitaxel [ethanol:Cremophor EL:5% (w/v) glucose (10:15:75%)] is well tolerated.

Figure 10:
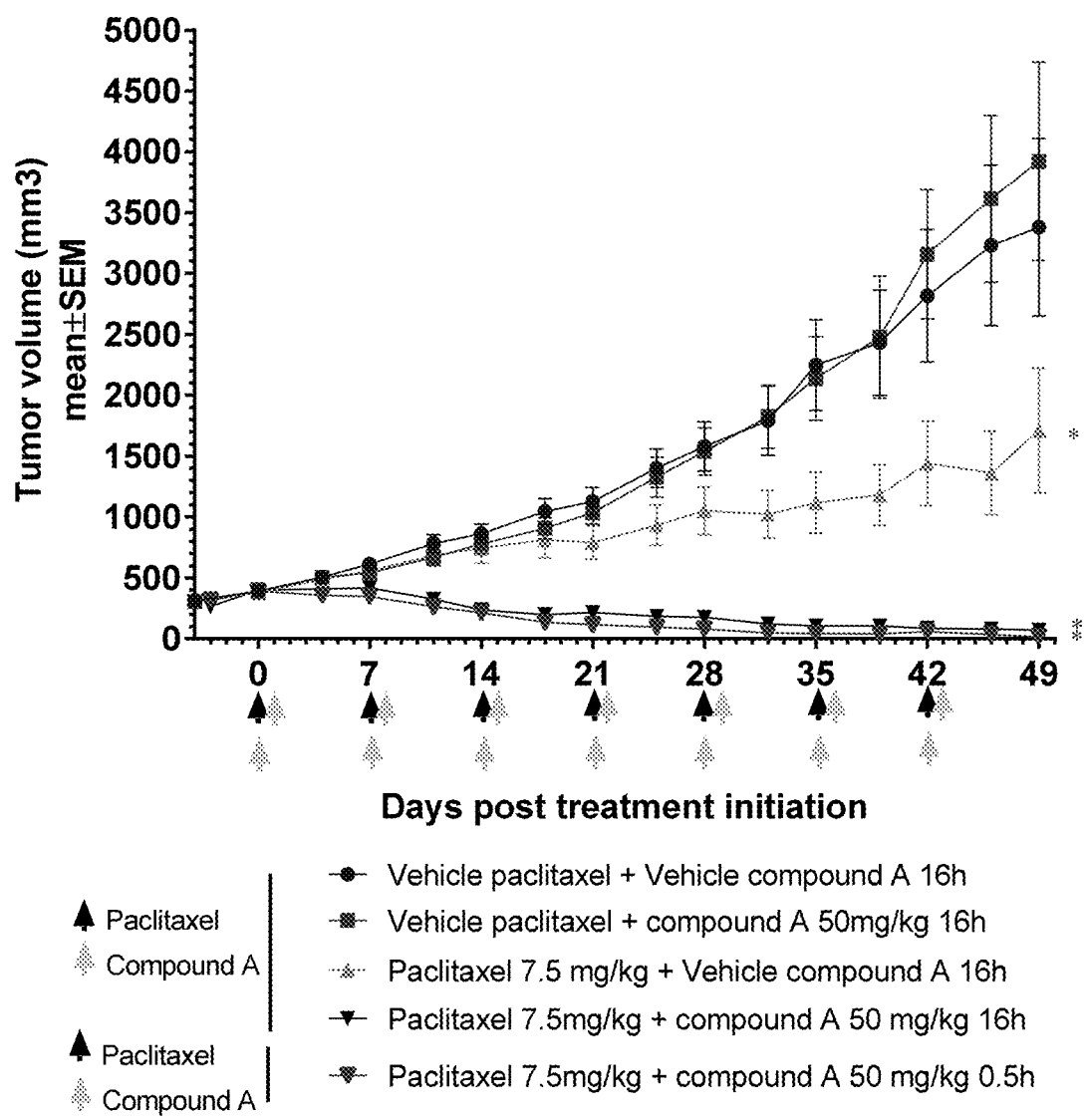
FIG. 10 illustrates efficacy of paclitaxel and Compound 1 (named as Compound A in the Figure) alone and in combination in female nude rats bearing MDA-MB-231 xenografts, a model of TNBC. Tumors were established in female nude rats by subcutaneous inoculation of human TNBC MDA-MB-231 cells (1×10$^7$ cells/200 µL HBSS/Matrigel 1:1 v/v). Animals with appropriate size tumors were randomized into groups (n=7-8) with a mean tumor volume about 400 mm$^3$. Tumor volumes were estimated using the two largest diameters according to (L×W$^2$×π/6) and body weights were measured 2-3 times per week. Data are presented as means±SEM or as individual tumor volumes. * p<0.05, compared with vehicle group (one way ANOVA with post hoc Dunnett's test).
Figure 12:
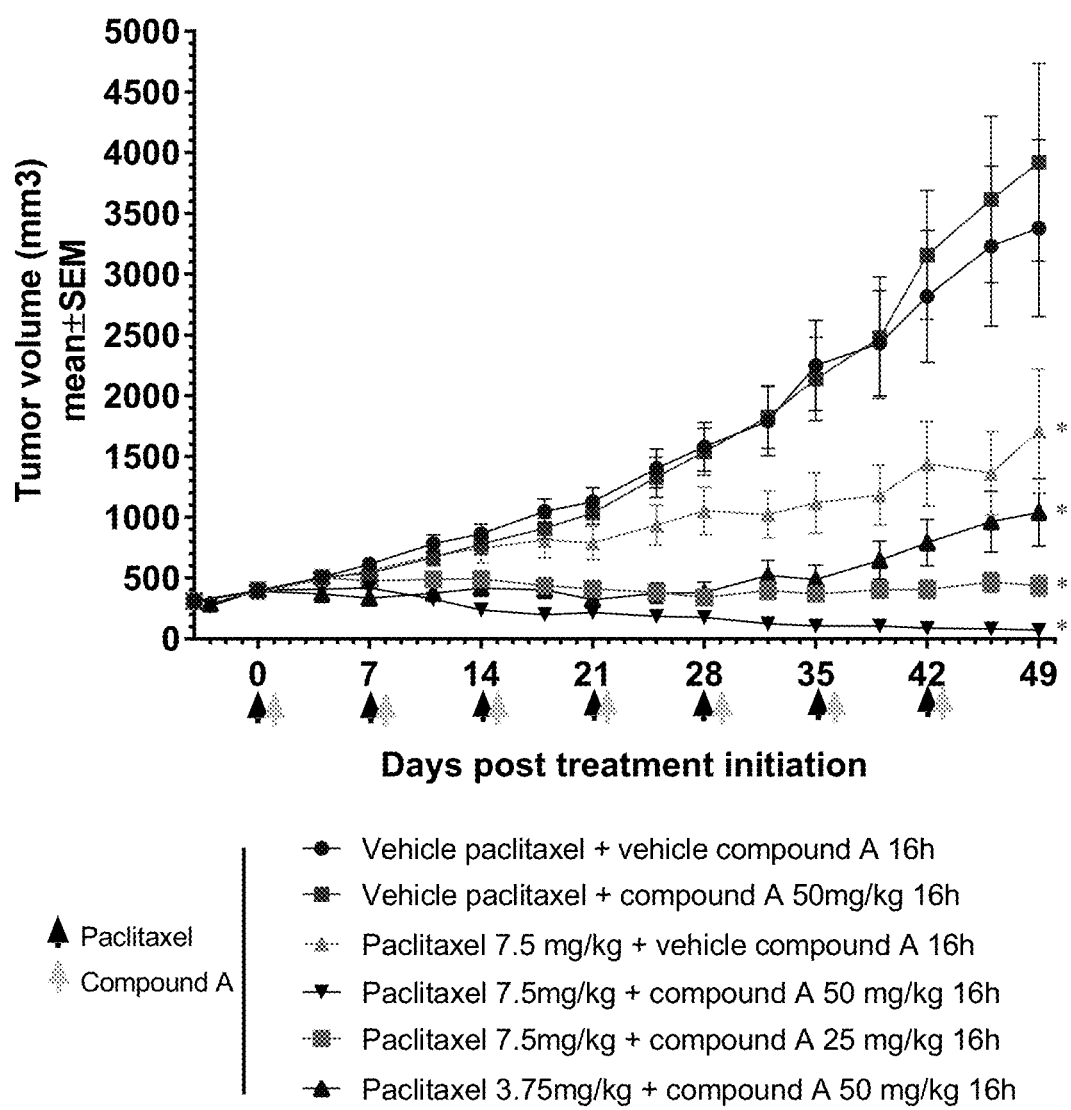
FIG. 12 illustrates efficacy of paclitaxel and Compound 1 (named as Compound A in the Figure) alone and in combination at different doses schedules in female nude rats bearing MDA-MB-231 xenografts, a model of TNBC. Tumors were established in female nude rats by subcutaneous inoculation of human TNBC MDA-MB-231 cells (1×10$^7$ cells/200 µL HBSS/Matrigel 1:1 v/v). Animals with appropriate size tumors were randomized into groups (n=7-8) with a mean tumor volume about 400 mm$^3$. Tumor volumes were estimated using the two largest diameters according to (L×W$^2$×π/6) and body weights were measured 2-3 times per week. Data are presented as means±SEM or as individual tumor volumes. * p<0.05, compared with vehicle group (one way ANOVA with post hoc Dunnett's test).

Compound 1 (50 mg/kg QW) in liposomal formulation exhibited no efficacy in the MDA-MB-231 xenograft model after QW×7 iv infusion administration (FIGS. 10 and 12).

Paclitaxel 7.5 mg/kg caused tumor growth delay (T/C %=34%) and was significantly (p<0.05) different from the vehicle treated group (FIGS. 10 and 12).

Combination of 7.5 mg/kg iv paclitaxel plus 50 mg/kg iv Compound 1 administered 0.5 h or 16 h apart caused 82 and 59% regression, respectively on day 28 after start of treatment in the surviving animals (3/8 in both groups) (FIG. 10). On day 46 from start of treatment, tumor regression was 92 and 81%, in the surviving animals 2/8 and 3/8, respectively. The tumor volume in animals from both of these combination groups was significantly different (p<0.05) from that in animals treated with paclitaxel or Compound 1 alone on day 28 and 46 (FIG. 10).

Combination of 7.5 mg/kg iv paclitaxel plus 25 mg/kg iv Compound 1 administered 16 h apart caused tumor stasis (15% regression on day 28 and the T/C % values was 2% on day 49 after start of treatment) in the surviving (7/7) animals (FIG. 12). This dose schedule was well tolerated based on body weight changes and clinical signs.

Figure 11:
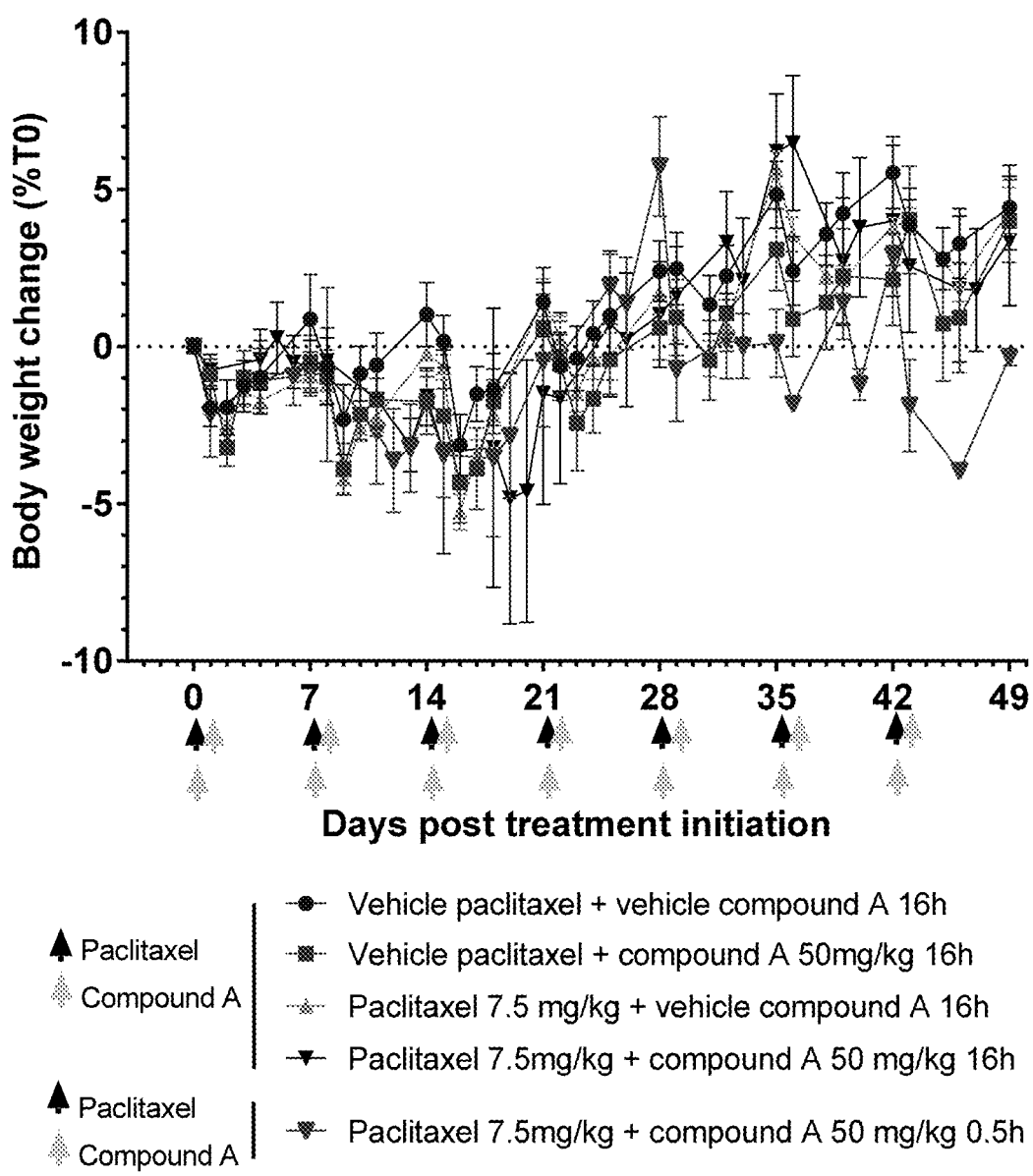
FIG. 11 illustrates tolerability of paclitaxel and Compound 1 (named as Compound A in the Figure) alone and in combination in female nude rats bearing MDA-MB-231 xenografts, a model of TNBC. Tumors were established in female nude rats by subcutaneous inoculation of human TNBC MDA-MB-231 cells (1×10$^7$ cells/200 µL HBSS/Matrigel 1:1 v/v). Animals with appropriate size tumors were randomized into groups (n=7-8) with a mean tumor volume about 400 mm$^3$. Tumor volumes were estimated using the two largest diameters according to (L×W$^2$×π/6) and body weights were measured 2-3 times per week.
Figure 13:
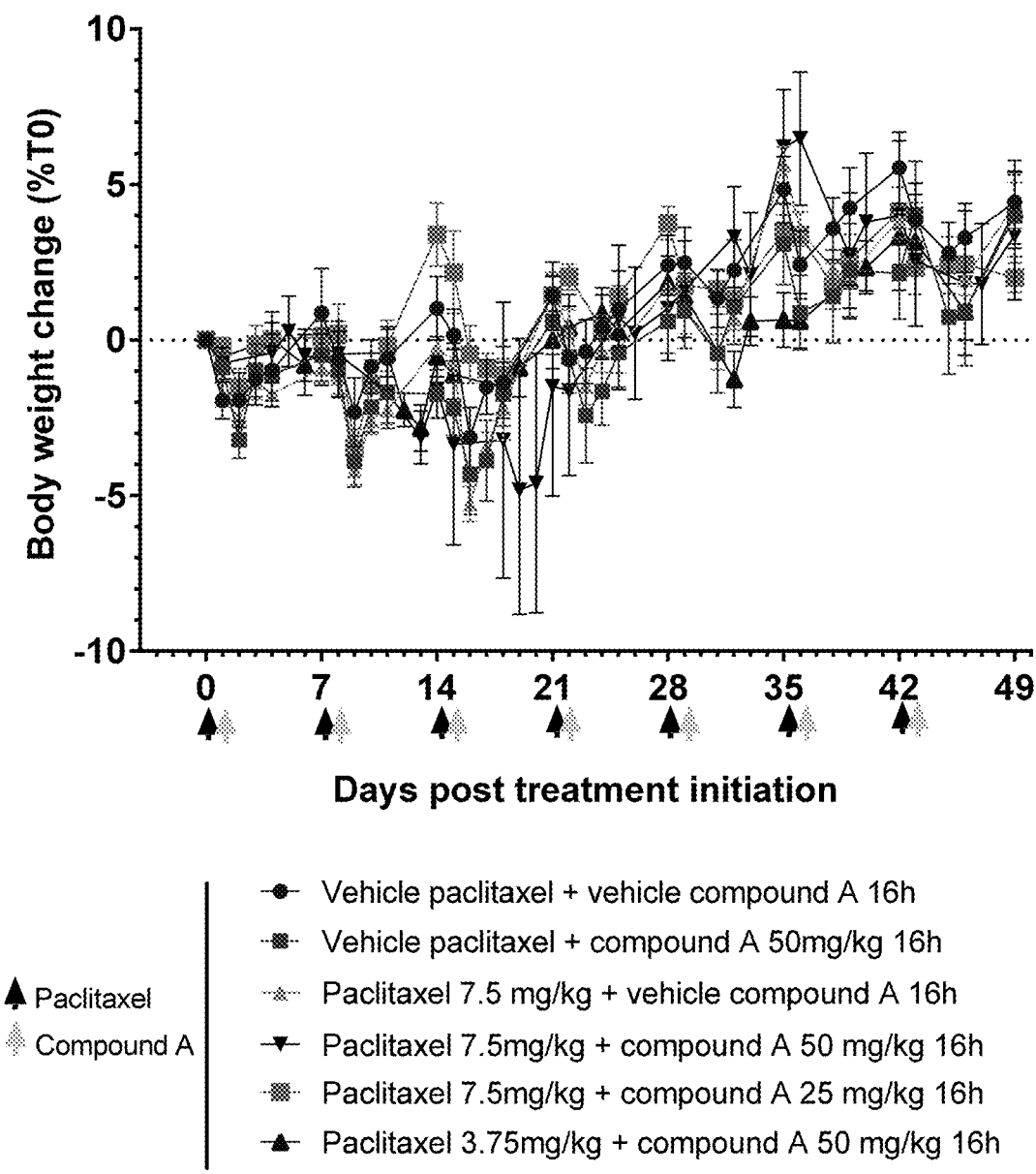
FIG. 13 illustrates tolerability of paclitaxel and Compound 1 (named as Compound A in the Figure) alone and in combination at different doses schedules in female nude rats bearing MDA-MB-231 xenografts, a model of TNBC. Tumors were established in female nude rats by subcutaneous inoculation of human TNBC MDA-MB-231 cells ($1\times10^7$ cells/200 µL HBSS/Matrigel 1:1 v/v). Animals with appropriate size tumors were randomized into groups (n=7-8) with a mean tumor volume about 400 mm$^3$. Tumor volumes were estimated using the two largest diameters according to $(L\times W^2\times\pi/6)$ and body weights were measured 2-3 times per week.

Combination of 3.75 mg/kg iv paclitaxel plus 50 mg/kg iv Compound 1 administered 16 h apart caused tumor stasis up to day 35 (3% regression on day 28 and the T/C % values was 20% on day 49 after start of treatment) in the surviving (7/7) animals (FIG. 12). This dose schedule was well tolerated based on body weight changes and clinical signs (FIGS. 11 and 13). These data indicate that combination of paclitaxel and Compound 1 has a marked positive effect on antitumor activity compared to either agent alone.

Example 7: MCL-1 Inhibition Sensitizes PDX Tumors to Taxane Treatment In Vivo

We determined the in vivo therapeutic effect of Compound 1 in combination therapy, in TNBC 110T PDX model.

Material and Method

Human breast cancer tissues were obtained from consenting patients through the Royal Melbourne Hospital Tissue Bank, the Victorian Cancer Biobank and Georges-Francois Leclerc Center with relevant institutional review board approval. Human Ethics approval was obtained from the Walter and Eliza Hall Institute (WEHI) Human Research Ethics Committee and from the Georges-Francois Leclerc Center Human Research Ethics Committee. NOD SCID IL2 gamma receptor knockout mice or SCID mice were bred and maintained according to institutional guidelines. All animal experiments were approved by the WEHI and Servier Research Institute (IdRS) Animal Ethics Committee.

A cohort of 40 female NSG mice was seeded with thawed single cell suspensions of early passage human breast tumors (TNBC PDX110). Briefly, 100,000 cells were resuspended in 10 μl of transplantation buffer (50% fetal calf serum, 10% of a 0.04% trypan blue solution and 40% PBS) and growth-factor-reduced Matrigel [BD] at a ratio of 3:1, and injected into the cleared mammary fat pads of 3- or 4-week-old NOD-SCID-IL2R$\gamma_c^{-/-}$ female mice. Mice were monitored for tumor development three times weekly and tumor size measured using electronic vernier calipers. Tumor volume was estimated by measuring the minimum and maximum tumor diameters using the formula: (minimum diameter)$^2$(maximum diameter)/2. Once tumors reached a volume of 60-110 mm$^3$, mice were randomized into treatment arms and treatment commenced. Docetaxel or its vehicle was prepared by dissolving stock solution (20 mg/ml) with PBS and injected i.p. every 21 days for two treatment cycles. The duration of therapy is indicated by the bar. Compound 1 was dissolved in 20% (2-Hydroxypropyl)-β-cyclodextrin and 25 mM hydrochloric acid. Compound 1 (15 mg/kg) or its vehicle was injected i.v. twice weekly for six weeks. Mice were sacrificed at the first measurement where tumor volume exceeded 600 mm$^3$, or if their health deteriorated for reasons other than disease progression or drug toxicity (censored event). n=9-10 mice per treatment group.

Results

Figure 14:
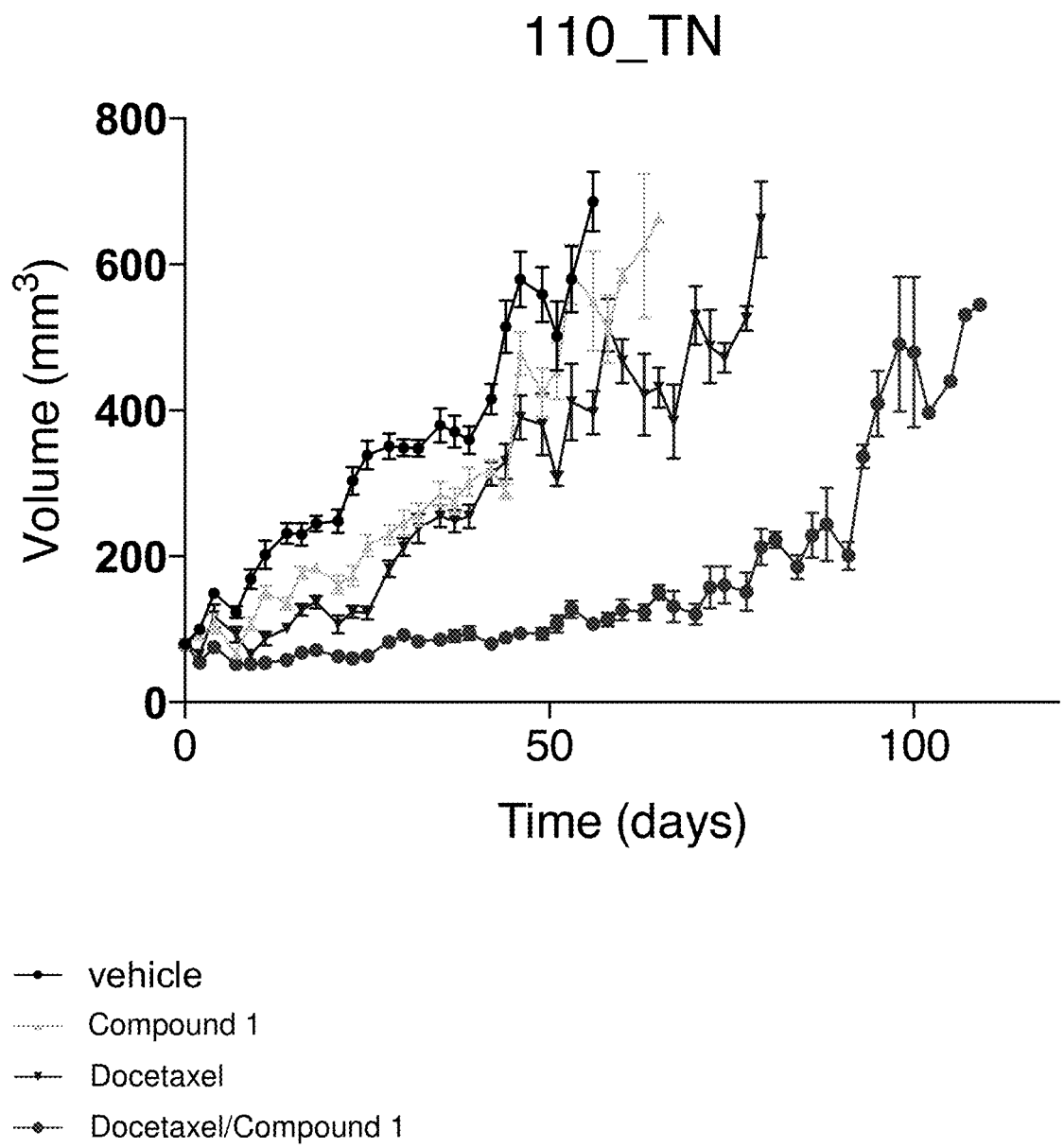
FIG. 14 illustrates synergistic effect of Compound 1 with docetaxel.

Compound 1 alone was insufficient in inhibiting tumor growth. However, we observed a superior activity in combination with docetaxel as compared to docetaxel administered as a single agent, resulting in significantly improved animal survival in the PDX model (FIG. 14).

These results indicate that MCL-1 inhibitors combined with taxane compounds are likely to significantly enhance tumor response and clinical outcome.

Example 8: Antitumor Activity of Docetaxel and Compound 1 in Female SCID Mice Bearing Patient Derived TNBC Model This study evaluated the antitumor activity Compound 1 in combination with docetaxel in a TNBC PDX model OD-BRE-00589, in female SCID mice.

Methods

Docetaxel was formulated in 5% ethanol, 5% PS80 and 90% Glucose at 0.67 mg/ml to administer 10 mg/kg. Compound 1 was formulated in a liposomal formulation (Novartis) at 7.5 mg/ml to administer 70 mg/kg.

OD-BRE-00589 is a triple negative breast cancer PDX, obtained from the IMODI consortium. Consenting patients was obtained from the Georges-Francois Leclerc Center Human Research Ethics Committee. It was grafted on SCID mice as fragments of 27 mm$^3$ volume.

Tumor growth was monitored regularly post fragment grafting and animals were randomized 11 days after grafting into treatment groups (n=8) with a mean tumor volume of about 200 mm$^3$. Control group was not treated and the other groups were treated with:
1) 70 mg/kg of Compound 1 iv, or
2) 10 mg/kg of docetaxel iv, or
3) 10 mg/kg of docetaxel iv followed by 30 min later with 70 mg/kg of Compound 1, or
4) 10 mg/kg of docetaxel iv followed by 72 h later with 70 mg/kg of Compound 1.

The administrations were performed once in the caudal vein.

Tumor volumes were measured using calipers 2-3 times per week. Tumor volume was calculated using the formula: length×width$^2$/2. Animals were also weighed 2-3 times per week and examined frequently for overt signs of any adverse effects.

Results

Figure 15:
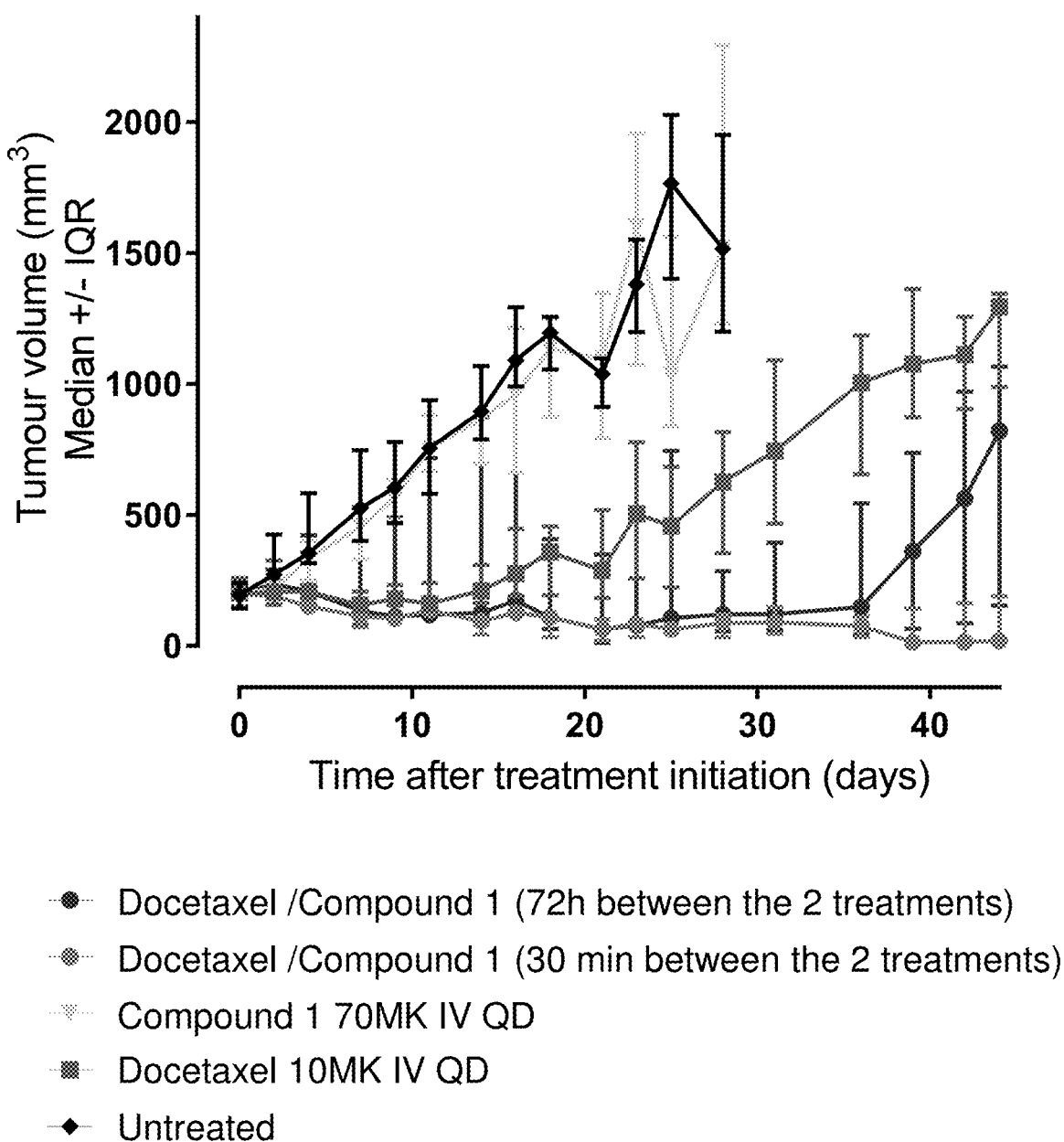
FIG. 15 illustrates antitumor activity of docetaxel and Compound 1 administrated IV alone and in combination in female SCID mice bearing patient derived TNBC model. Docetaxel was administrated first followed either 30 minutes or 72 hours later with Compound 1.

Compound 1 alone was insufficient in inhibiting tumor growth. However, we observed a superior activity in combination with docetaxel as compared to docetaxel administered as a single agent, resulting in significantly improved antitumor activity in the PDX model (FIG. 15).

These results indicate that MCL-1 inhibitors combined with taxane compounds are likely to significantly enhance tumor response and clinical outcome.

Example 9: Efficacy Studies of Compound 1 Combined to Paclitaxel in PDX Models Resistant to Docetaxel Methods PDX models whose resistance to docetaxel has been confirmed in vivo were tested. Each treatment group included 5 female Swiss Nude mice, aged from 6 to 8 weeks old. The treatment started when xenografts reached a mean tumor volume of ~120-150 mm$^3$. Groups of mice were then randomly affected to the different treatments. The number of grafted animals depended on the homogeneity of the tumor growth.

Formulated in a liposomal formulation, Compound 1 was administered intravenously at 70 mg/kg once a week. The formulation had to be prepared extemporaneously. Paclitaxel diluted in 0.9% NaCl was given ip at 25 mg/kg. Paclitaxel was given QW 16 hours before the administration of Compound 1. The administration schedule of the different treatments is defined as follows:

| Group | Dose (mg/kg) | Schedule |
|---|---|---|
| Control (vehicle) | — | — |
| Compound 1 | 70 | IV, Q7D, 4w: D 1-D 8-D 15-D 22 |
| Paclitaxel | 25 | IP, Q7D, 4w: D 1-D 8-D 15-D 22 |
| Compound 1 + paclitaxel | Compound 1: 70 Paclitaxel: 25 | Q7D, 4w Paclitaxel, IP: D 1-D 8-D 15-D 22 Compound 1, IV: D 1-D 8-D 15-D 22 |

Tumor sizes were measured twice a week and weights of individual mice were measured once a week. Treatments were done until the median tumor volume of the most responsive group started to regrow. Mice were followed after the stop of the treatment to compare the time to relapse between the groups. Using Statview software, tumor volume and/or relative tumor volume (RTV, ratio of the volume at the time t divided by the initial volume at day 1 and multiplied by 100), optimal growth inhibition (ratio of RTV (×100) in the treated group divided by the RTV in the controls), growth delay (the time in days necessary to multiply by 4 an initial tumor volume of 200 mm$^3$ in treated group and control group) and body weight change were compared.

If relapse was observed after paclitaxel treatment, tumors were rechallenged with the Compound 1+paclitaxel combination. This was done either by including 10 mice in the paclitaxel treated group and then treated tumor relapsing mice with paclitaxel alone (5 animals) or in combination (5 animals), or by using not randomized mice from the efficacy study. If initial response to paclitaxel was observed, additional animals left after randomization were included for this study.

Results

Compound 1 alone was insufficient in inhibiting tumor growth. However, we observed a superior activity in combination with paclitaxel as compared to paclitaxel administered as a single agent, resulting in significantly improved antitumor activity in the PDX model resistant to a taxane compound.

These results indicate that MCL-1 inhibitors combined with taxane compounds are likely to significantly enhance tumor response and clinical outcome.

The invention claimed is:

1. A combination comprising:
    (a) an MCL-1 inhibitor which is (2R)-2-{[(5S$_a$)-5-{3-chloro-2-methyl-4-[2-(4-methylpiperazin-1-yl)ethoxy]phenyl}-6-(5-fluorofuran-2-yl)thieno{2,3-d]pyrimidin-4-yl]oxy}-3-(2-{[-(2,2,2-trifluoroethyl)-1H-pyrazol-5-yl]methoxy}phenyl)propanoic acid or (2R)-2-{[5S$_a$)-5-{3-chloro-2-methyl-4-[2-(4-methylpiperazin-1-yl)ethoxy]phenyl}-6-(4-fluorophenyl)thieno [2,3-d]pyrimidin-4-yl]oxy}-3-(2-{[2-(2-methoxyphenyl)pyrimidin-4-yl]methoxy}phenyl)propanoic acid
    or an addition salt thereof with a pharmaceutically acceptable acid or base,
    and (b) a taxane compound which is paclitaxel or docetaxel.

2. The combination according to claim 1, wherein the MCL-1 inhibitor is (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid.

3. The combination according to claim 1, wherein the MCL-1 inhibitor is (2R)-2-{[(5S$_a$)-5-{3-chloro-2-methyl-4-[2-(4-methylpiperazin-1-yl)ethoxy]phenyl}-6-(4-fluorophenyl)thieno [2,3-d]pyrimidin-4-yl] oxy}-3-(2-{[2-(2-methoxyphenyl)pyrimidin-4-yl]methoxy}phenyl)propanoic acid.

4. The combination according to claim 3, wherein the (2R)-2-{[(5S$_a$)-5-{3-chloro-2-methyl-4-[2-(4-methylpiperazin-1-yl)ethoxy]phenyl}-6-(4-fluorophenyl)thieno [2,3-d] pyrimidin-4-yl]oxy}-3-(2-{[2-(2-methoxyphenyl)pyrimidin-4-yl]methoxy}phenyl)propanoic acid is present at a dosage from 25 mg to 1500 mg.

5. The combination according to claim 1, further comprising one or more excipients.

6. A pharmaceutical composition comprising the combination according to claim 1, in combination with one or more pharmaceutically acceptable excipients.

7. The pharmaceutical composition according to claim 6, which is packaged for simultaneous, sequential or separate administration.

8. A method of treating cancer in a subject in need thereof, comprising administration of an effective amount of the combination according to claim 1, alone or in combination with one or more pharmaceutically acceptable excipients.

9. The method according to claim 8, wherein the MCL-1 inhibitor and the taxane compound are administered in amounts which are jointly therapeutically effective for the treatment of cancer.

10. The method according to claim 8, wherein the MCL-1 inhibitor and the taxane compound are administered in amounts which are synergistically effective for the treatment of cancer.

11. The method according to claim 8, wherein the MCL-1 inhibitor and the taxane compound are administered in synergistically effective amounts which enable a reduction of the dose required for each compound in the treatment of cancer, whilst providing an efficacious cancer treatment, with eventually a reduction in side effects.

12. The method according to claim 8, wherein the cancer is breast cancer.

13. The method according to claim 8, wherein the cancer is lung cancer.

14. The method according to claim 8, wherein the MCL-1 inhibitor is administered once a week.

15. The method according to claim 8, wherein the MCL-1 inhibitor and the taxane compound are administered intravenously.

16. The method according to claim 8, wherein the MCL-1 inhibitor is administered orally and the taxane compound is administered intravenously.

\* \* \* \* \*

UNITED STATES PATENT AND TRADEMARK OFFICE
CERTIFICATE OF CORRECTION

PATENT NO. : 10,765,680 B2  
APPLICATION NO. : 16/475389  
DATED : September 8, 2020  
INVENTOR(S) : Dale Porter et al.

It is certified that error appears in the above-identified patent and that said Letters Patent is hereby corrected as shown below:

On the Title Page

Column 1, Assignees: In the first assignee, LABORATORIES should read LABORATOIRES.

Column 2, Other Publications: Line 8 should read PCT/EP2018/050298.

Signed and Sealed this  
Tenth Day of November, 2020

Andrei Iancu  
*Director of the United States Patent and Trademark Office*